US012796894B2

(12) United States Patent
Yuan et al.

(10) Patent No.: US 12,796,894 B2
(45) Date of Patent: Nov. 17, 2026

(54) SYSTEMS AND METHODS FOR SCALABLE FABRICATION OF HIGH-PERFORMANCE OPTICAL COHERENCE TOMOGRAPHY ENDOSCOPES USING LIQUID SHAPING TECHNIQUE

(71) Applicant: The Chinese University of Hong Kong, Hong Kong (CN)

(72) Inventors: Wu Yuan, Hong Kong (CN); Chao Xu, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 154 days.

(21) Appl. No.: 18/775,087

(22) Filed: Jul. 17, 2024

(65) Prior Publication Data

US 2025/0089995 A1 Mar. 20, 2025

Related U.S. Application Data

(60) Provisional application No. 63/538,716, filed on Sep. 15, 2023.

(51) Int. Cl.
*A61B 1/00* (2006.01)
*A61B 1/07* (2006.01)

(52) U.S. Cl.
CPC ........ *A61B 1/0011* (2013.01); *A61B 1/00096* (2013.01); *A61B 1/00103* (2013.01); *A61B 1/07* (2013.01)

(58) Field of Classification Search
CPC ............ A61B 1/00096; A61B 1/00103; A61B 1/0011; A61B 1/07; A61B 5/0066; B29D 11/00365; G02B 23/2423
See application file for complete search history.

(56) References Cited

PUBLICATIONS

Swanson, E.A., et al., "The ecosystem that powered the translation of OCT from fundamental research to clinical and commercial impact [Invited]," Biomedical Optics Express, Mar. 1, 2017, 8(3):1638-1664.
Zhu, X., et al., "Fabrication of multi-scale micro-lens arrays on hydrophobic surfaces using a drop-on-demand droplet generator," Optics & Laser Technology, 2015, 66:156-165.
Xu, C., et al., "Submillimeter robotic OCT neuroendoscope for deep-brain imaging in vivo," Advanced Biomedical and Clinical Diagnostic and Surgical Guidance Systems XXII, 2024, 12831:1-4.

(Continued)

*Primary Examiner* — Michael T Rozanski
(74) *Attorney, Agent, or Firm* — SALIWANCHIK, LLOYD & EISENSCHENK

(57) ABSTRACT

Endoscopic optical coherence tomography (OCT) provides diagnostic images of internal organs and guides interventions in real-time. A liquid shaping method and system are provided for the rapid and scalable fabrication of high-performance OCT endoscopes working at various wavelength ranges. The method and systems enable the flexible customization of freeform lenses with sub-nanometer optical surface roughness by regulating the minimum energy state of curable optical liquid on a wettability-modified substrate and precisely controlling the liquid volume and physical boundary on a substrate. As a result, multiple endoscopes, for example, 800-nm OCT endoscopes with a diameter of approximately 0.6 mm including both rigid and flexible endoscopes, can be simultaneously fabricated. The liquid shaping method and systems offer new approaches for mass production of cost-effective and high-performance OCT endoscopes.

7 Claims, 39 Drawing Sheets

(56) References Cited

PUBLICATIONS

Xu, C., et al., "Aberration-corrected High-resolution OCT Microprobe Using Liquid-shaped Freeform Microlens," Frontiers in Optics + Laser Science, 2024, pp. 1-2.
Xu, C., et al., "Miniature ultrahigh-resolution visible-light OCT endoscopy," Endoscopic Microscopy XIX, 2024, 12820:1-4.
Xu, C., et al., "Patient-Mounted Neuro Optical Coherence Tomography for Targeted Minimally Invasive Micro-Resolution Volumetric Imaging in Brain In Vivo," Advanced Intelligent Systems, 2024, 2400488:1-13.
Xu, C., et al., "Liquid-shaped microlens for scalable production of ultrahigh-resolution optical coherence tomography microendoscope," Communications Engineering, 2024, 3:1-12.
Xu, C., et al., "Ultrathin visible-light OCT endomicroscopy for in vivo ultrahigh-resolution neuroimaging in deep brain," APL Photonics, Nov. 5, 2024, 9(110804):1-10.
Lee, S. Y., et al., "Microlens With Tunable Astigmatism," IEEE Photonics Technology Letters, Sep. 15, 2007, 19(18):1383-1385.
Fujimoto, J. G., "Optical coherence tomography for ultrahigh resolution in vivo imaging," Nature Biotechnology, Nov. 2003, 21(11):1361-1367.
Adler, D. C., et al., "Three-dimensional endomicroscopy using optical coherence tomography," Nature Photonics, Dec. 2007, 1:709-716.
Syed, S. H., et al., "Optical coherence tomography for high-resolution imaging of mouse development in utero," Journal of Biomedical Optics, Apr. 2011, 16(4):1-7.
Larin, K. V., et al., "Optical Clearing for OCT Image Enhancement and In-Depth Monitoring of Molecular Diffusion," IEEE Journal of Selected Topics in Quantum Electronics, May-Jun. 2012, 18(3):1244-1259.
Lin, N. C., et al., "Scanning optical coherence tomography probe for in vivo imaging and displacement measurements in the cochlea," Biomedical Optics Express, Feb. 1, 2019, 10(2):1032-1043.
Yu, X., et al., "Real-time assessment of catheter contact and orientation using an integrated optical coherence tomography cardiac ablation catheter," Applied Optics, May 10, 2019, 58(14):3823-3829.
Yuan, W., et al., "Optimal operational conditions for supercontinuum-based ultrahigh-resolution endoscopic OCT imaging," Optics Letters, Jan. 15, 2016, 41(2):250-253.
Yuan, W., et al., "Super-achromatic monolithic microprobe for ultrahigh-resolution endoscopic optical coherence tomography at 800 nm," Nature Communications, Nov. 16, 2017, 8:1-9.
Yuan, W., et al., "In vivo assessment of inflammatory bowel disease in rats with ultrahigh-resolution colonoscopic OCT," Biomedical Optics Express, Apr. 1, 2022, 13(4):2091-2102.
Thiboutot, J., et al., "Visualization and validation of the microstructures in the airway wall in vivo using diffractive optical coherence tomography," Academy Radiology, 2022, pp. 1-17.
Yuan, W., et al., "Direct Visualization and Quantitative Imaging of Small Airway Anatomy In Vivo Using Deep Learning Assisted Diffractive OCT," IEEE Transactions on Biomedical Engineering, 2024, pp. 1-19. [Author Manuscript].
Luo, H., et al., "Human colorectal cancer tissue assessment using optical coherence tomography catheter and deep learning," Journal of Biophotonics, Jun. 2022, 15(6):1-18. [Author Manuscript].
Kim, J., et al., "Flexible endoscopic micro-optical coherence tomography for three-dimensional imaging of the arterial microstructure," Scientific Reports, 2020, 10(9248):1-11.
Zeng, X., et al., "Ultrahigh-resolution optical coherence microscopy accurately classifies precancerous and cancerous human cervix free of labeling," Theranostics, Apr. 30, 2018, 8(11):3099-3110.
Ma, Y., et al., "Computer-Aided Diagnosis of Label-Free 3-D Optical Coherence Microscopy Images of Human Cervical Tissue," IEEE Transactions on Biomedical Engineering, Sep. 2019, 66(9):2447-2456.
Ren, C., et al., "Multi-center clinical study using optical coherence tomography for evaluation of cervical lesions in-vivo," Scientific Reports, 2021, 11(7507):1-9.
Li, J., et al., "Ultrathin monolithic 3D printed optical coherence tomography endoscopy for preclinical and clinical use," Light: Science & Applications, 2020, 9(124):1-10.
Yuan, W., et al., "Theranostic OCT microneedle for fast ultrahigh-resolution deep-brain imaging and efficient laser ablation in vivo," Science Advances, Apr. 10, 2020, 6:1-9.
Keenan, M., et al., "Design and characterization of a combined OCT and wide field imaging falloposcope for ovarian cancer detection," Biomedical Optics Express, Jan. 1, 2017, 8(1):124-136.
Li, J., et al., "3D-Printed Micro Lens-in-Lens for In Vivo Multimodal Microendoscopy," Small, 2022, 18:1-8.
Cadarso, V. J., et al., "Microlenses with defined contour shapes," Optics Express, Sep. 9, 2011, 19(19):18665-18670.
Roy, A. C., et al., "Generation of Aspherical Optical Lenses via Arrested Spreading and Pinching of a Cross-Linkable Liquid," Langmuir, 2016, pp. 1-9.
Roy, A. C., et al., "Bi-convex aspheric optical lenses," Applied Physics Letters, 2017, 110:1-6.
Chen, C. T., et al., "Self-aligned hemispherical formation of microlenses from colloidal droplets on heterogeneous surfaces," Journal of Micromechanics and Microengineering, 2009, 19:1-10.
Kim, J. Y., et al., "Inkjet-Printed Multicolor Arrays of Highly Luminescent Nanocrystal-Based Nanocomposites," Small, 2009, 5(9):1051-1057.
Pataky, K., et al., "Microdrop Printing of Hydrogel Bioinks into 3D Tissue-Like Geometries," Advanced Materials, 2012, 24:391-396.
Elgarisi, M., et al., "Fabrication of freeform optical components by fluidic shaping," Optica, Nov. 2021, 8(11):1501-1506.
Eshel, R., et al., "Programmable thermocapillary shaping of thin liquid films," Flow, 2022, 2:1-13.
Ikawa, M., et al., "Simple push coating of polymer thin-film transistors," Nature Communications, Nov. 6, 2012, 3(1176):1-8.
Ganesh, V.A., et al., "Superhydrophobic fluorinated POSS-PVDF-HFP nanocomposite coating on glass by electrospinning," Journal of Materials Chemistry, 2012, 22: 18479-18485.
Clarke, A., et al., "Spreading and Imbibition of Liquid Droplets on Porous Surfaces," Langmuir, 2002, 18(8):2980-2984.
Maruno, T., et al., "Properties of a UV-curable, durable precision adhesive," Journal of Adhesion Science and Technology, 1995, 9(10):1-15.
Takahashi, A., et al., "Volume change and viscoelastic properties of UV-curable adhesives for precise positioning during curing process and their formulation," The Journal of Adhesion, 2021, pp. 1-17.
An, J., et al.,"Gastroesophageal reflux GWAS identifies risk loci that also associate with subsequent severe esophageal diseases," Nature Communications, Sep. 16, 2019, 10(4219):1-10.
Chen, Y., et al., "Ultrahigh resolution optical coherence tomography of Barrett's esophagus: preliminary descriptive clinical study correlating images with histology," Endoscopy, 2007, 39:599-605.
Wilder-Smith, C. H., et al.,"Quantification of Dental Erosions in Patients With GERD Using Optical Coherence Tomography Before and After Double-Blind, Randomized Treatment With Esomeprazole or Placebo," American Journal of Gastroenterology, Nov. 2009, 104:2788-2795.
Prati, F., et al., "Expert review document on methodology, terminology, and clinical applications of optical coherence tomography: physical principles, methodology of image acquisition, and clinical application for assessment of coronary arteries and atherosclerosis," European Heart Journal, 2010, 31:401-415.
Yoo, H., et al., "Intra-arterial catheter for simultaneous microstructural and molecular imaging in vivo," Nature Medicine, Dec. 2011, 17(12):1680-1685.
Zhai, M., et al., "Extracellular traps from activated vascular smooth muscle cells drive the progression of atherosclerosis," Nature Communications, Dec. 6, 2022, 13:1-15.
Araki, M., et al., "Optical coherence tomography in coronary atherosclerosis assessment and intervention," Nature Reviews Cardiology, Oct. 2022, 19(10):1-36. [Author Manuscript].

(56) References Cited

PUBLICATIONS

Tahara, S., et al., "Intravascular Optical Coherence Tomography Detection of Atherosclerosis and Inflammation in Murine Aorta," Arteriosclerosis Thrombosis and Vascular Biology, 2012, 32: 1150-1157.
Nakashima, Y., et al., "Early atherosclerosis in humans: role of diffuse intimal thickening and extracellular matrix proteoglycans," Cardiovascular Research, 2008, 79:14-23.
Zhang, X., et al., "Modeling early stage atherosclerosis in a primary human vascular microphysiological system," Nature Communications, 2020, 11:1-17.
Boua, P. R., et al., "Genetic associations with carotid intima-media thickness link to atherosclerosis with sex-specific effects in sub-Saharan Africans," Nature Communications, 2022, 13:1-11.
Bohringer, H. J., et al., "Time-Domain and Spectral-Domain Optical Coherence Tomography in the Analysis of Brain Tumor Tissue," Lasers in Surgery and Medicine, May 30, 2006, 38:588-597.
Tsytsarev, V., et al., "Photoacoustic and optical coherence tomography of epilepsy with high temporal and spatial resolution and dual optical contrasts," Journal of Neuroscience Methods, 2013, 216:142-145.
Liu, Q., et al., ". Monitoring acute stroke in mouse model using laser speckle imaging-guided visible-light optical coherence tomography," IEEE Transactions on Biomedical Engineering, 2018, pp. 1-7.
Beckmann, L., et al., "Longitudinal deep-brain imaging in mouse using visible-light optical coherence tomography through chronic microprism cranial window," Biomedical Optics Express, Oct. 1, 2019, 10(10):5235-5250.
Ni, X., et al., "Soft shape-programmable surfaces by fast electromagnetic actuation of liquid metal networks," Nature Communications, 2022, 13:1-9.

SYSTEMS AND METHODS FOR SCALABLE FABRICATION OF HIGH-PERFORMANCE OPTICAL COHERENCE TOMOGRAPHY ENDOSCOPES USING LIQUID SHAPING TECHNIQUE

CROSS-REFERENCE TO RELATED APPLICATION

This application claims the benefit of U.S. Patent Application Ser. No. 63/538,716, filed Sep. 15, 2023, which is hereby incorporated by reference in its entirety including any tables, figures, or drawings.

FIELD OF ART

The present invention pertains to endoscopes and fabrication techniques.

BACKGROUND

Optical coherence tomography (OCT) combines features of both ultrasound and confocal microscopy, bridging the gap between these two imaging modalities. While ultrasound imaging offers deep imaging depth of centimeters, it is limited in resolution of about hundreds of micrometers. In contrast, confocal microscopy provides submicron resolution, but its imaging depth is restricted to at most one hundred micrometers in tissue. OCT technology addresses these limitations. It provides an axial resolution ranging from 1 to 10 m and an imaging depth of about 1-3 mm in tissue. As a result, OCT is particularly suitable for high-resolution imaging of shallow tissue layers, such as the mucosa of luminal organs.

As one of the premier clinical applications, endoscopic OCT has emerged as a valuable tool for providing diagnostic images of internal lumens. This technique allows the near-histologic quality visualization of tissue microstructures and provides histopathological information. It overcomes the limitations of traditional biopsy by enabling three-dimensional (3D) volumetric sampling across a large area without necessitating tissue removal. In clinical practice, the imaging in luminal organs requires the use of high-performance disposable OCT endoscopes to accurately resolve fine pathological changes associated with diseases, for example, the fibrous cap of atherosclerosis.

Current disposable OCT endoscopes are mainly fabricated using graded-index (GRIN) lens/fiber or fiber ball lens. However, the OCT endoscope composed of GRIN lens/fiber exhibits significant chromatic and spherical aberrations, especially in short wavelength range (such as 800 nm and visible light range). Alternatively, an achromatic OCT endoscope can be developed using a distal fiber-melted ball lens. However, the fiber-melting technique lacks the necessary flexibility to customize a ball lens that achieves an optimal balance between working distance, resolution, and depth of focus (DOF). The fabrication of a reflective surface on a fiber ball lens involves a labor-intensive angle-polishing procedure, which poses challenges in achieving the desired optical surface roughness. Furthermore, both fabrication methods require time-consuming and complex assembly procedures, including high-precision optical alignments, and necessitate well-trained specialists. As a result, conventional fabrication methods still lack scalability and incur high adoption costs in clinical settings. More recently, two-photon 3D printing has been used to create freeform side-deflecting optics on the tip of single-mode fiber (SMF), enabling the development of a 1,300-nm OCT endoscope with a diameter of around 0.5 mm. However, this technique is costly and lacks scalability. Additionally, the surface roughness of 3D-printed optics, ranging from 10 to 200 nm, is suboptimal for OCT imaging.

Therefore, it is imperative to develop new methods for scalable fabrication of cost-effective and high-performance OCT endoscopes. There is a need for improved OCT endoscopes and methods of fabrication that allow for mass production (for low cost) and customization (for highly customizable performance to meet diverse clinical application needs).

BRIEF SUMMARY

In one aspect, the invention pertains to a liquid shaping-based method and system for the scalable fabrication of low-cost disposable OCT endoscopes of highly customizable performance.

In a first aspect, the invention pertains to methods based on a liquid shaping technique that facilitates fast and mass production of self-assembled freeform optics (including the lens and mirror) of sub-nanometer surface roughness and customized shapes and structures to effectively correct optical aberrations and provide the desired imaging performance.

In a second aspect, the invention pertains to an automated fabrication system that enables the fast assembly of freeform optics to the fiber probe of an OCT endoscope, eliminating the costly and time-consuming fabrication procedures, such as lens polishing. Additionally, the fabrication system does not require high-precision optical alignment and needs minimal human expertise in operation.

In some embodiments, a novel liquid shaping technique is provided that facilitates the rapid simultaneous fabrication of predesigned side-focusing lenses on fiber tips for use in ultrahigh-resolution OCT endoscopy. By regulating the minimum energy state of curable optical liquid on a substrate surface with tailored wetting properties, as well as controlling the droplet's volume and its physical boundary on the substrate, the size and shape of the distal lens of an OCT probe can be flexibly customized. This helps correct optical aberrations and optimize imaging performance. This technique also eliminates the need for angle-polishing and results in a liquid-shaped lens with sub-nanometer surface roughness. Using this technique, aberration-corrected OCT endoscopes can be fabricated simultaneously. As a prime example, the resulting endoscopes had a diameter of approximately 0.6 mm (including a protective sheath) and provided an ultrahigh resolution of 2.4 μm×4.5 μm (in axial and transverse directions, respectively). Furthermore, imaging performance, mechanical flexibility, and minimal invasiveness of these endoscopes were demonstrated by imaging the esophagus of rats and the aorta and brain of mice. The method further facilitates scalable fabrication of cost-effective, high-performance OCT endoscopes for minimally invasive and ultrahigh-resolution optical biopsies in clinical settings.

BRIEF DESCRIPTION OF THE DRAWINGS

FIGS. 1A-1G are schematic illustrations of optical lens fabrication using liquid shaping technique, wherein FIG. 1A depicts production of lens on a wettability-modified substrate using a piezoelectrically actuated dispenser with thermal control, FIG. 1B depicts OCT endoscope based on liquid-shaped lens for in vivo imaging in small and convoluted luminal organs, such as coronary vasculature, FIGS. 1C and 1D are schematics of optical liquid on a substrate (without physical boundary). The lenses of the same liquid volume ($V_1$) on the substrates of different wettability ($W_1$-$W_3$) have a different radius, i.e., $r_1$-$r_3$, and contact angle, i.e., $\theta_1$-$\theta_3$, wherein as the liquid volume increases from $V_1$ to $V_3$ on the substrate of the same wettability $W_4$, the radius of lens increases from $r_4$ to $r_6$ while maintaining a contact angle of $\theta_4$, FIG. 1E depicts production of spheroid lens using a substrate with a circular boundary. The radii and contact angles of lenses made with different liquid volumes are indicated with $r_1$, $r_2$, and $\theta_1$, $\theta_2$, $\theta_3$, respectively, FIG. 1F depicts fabrication of ellipsoid lens on a substrate with an elliptical boundary. The semi-major length, i.e., $m_1$, $m_2$, $m_3$, semi-minor length, i.e., $n_1$ and $n_2$, contact angle on x-z plane from $\theta_{x1}$ to $\theta_{x3}$, and contact angle on y-z plane from $\theta_{y1}$ to $\theta_{y3}$ of the lenses are illustrated when different liquid volumes are used on the substrate. Please note that $n_1$=$m_1$, $n_2$=$m_2$, $\theta_{x1}$=$\theta_{y1}$, and $\theta_{x2}$=$\theta_{y2}$, FIG. 1G depicts fabrication of spheroid lens with its shape actively controlled by temperature $T_1$-$T_3$. The substrates have the same wettability $W_5$ before applying thermal control. After the temperature increases from $T_1$ to $T_3$, the optical liquid with a volume of $V_5$ shows a decrease in contact angle from $\theta_5$ to $\theta_7$, in accordance with some embodiments of the subject invention.

FIGS. 2A-2G depict shape and size control of the lens using liquid shaping technique, wherein FIG. 2A depicts the contact angles and sizes (in radius and height) of lenses (illustrated in cross-sections) regulated by the wettability of glass substrate (without physical boundary) while using a constant liquid volume of about 50 nL, FIG. 2B depicts the lenses of constant 90° contact angle (in cross-sectional view) with their sizes (in radius and height) controlled by the droplet volumes from 5 nL to 800 nL, FIG. 2C depicts comparison of measured and theoretically calculated radii of lenses regulated by the liquid volume on the substrates of different wettability (indicated with colors). The green triangle represents the same set of measurements shown in FIG. 2B. The insets show three representative lenses of contact angles and radii of about 50°/440 μm, 75°/334 μm, and 90°/277 μm, respectively. Scale bars are 250 μm, FIG. 2D depicts cross-sectional profiles of semi-spherical lenses made on a substrate of a circular boundary (i.e., a radius of 493 μm), FIG. 2E depicts cross-sectional profiles of ellipsoid lenses fabricated on a substrate of an elliptical boundary (i.e., a semi-major length of 460 μm and a semi-minor length of 360 μm), the shapes and sizes of lenses are displayed on both x-z (colored solid lines) and y-z planes (colored dashed lines), FIG. 2F depicts cross-sectional profiles of the spheroid lens (about 50 nL in volume) made on a glass substrate with the same chemical wettability treatment but additional thermal control. As the increase of temperature, the contact angle of the resultant lens decreases, while its radius increases, and FIG. 2G depicts study of the shrinkage effect in lenses (in terms of contact angle and volume) by comparing their cross-sectional profiles before (colored solid lines) and after (colored dotted lines) ultraviolet light-induced polymerization. The shrinkage ratio is calculated using $(V_1-V_2)/V_1$, where $V_1$ and $V_2$ are the lens volume before and after polymerization, in accordance with some embodiments of the subject invention.

FIG. 3B depicts calculated back-reflection in endoscope versus NCF length L for four representative combinations of lens radius r and incident angle θ. The back-reflection is found to decrease by about 0.55 dB (black line), 0.33 dB (red line), 0.89 dB (blue line), and 0.41 dB (green line), respectively, as NCF length L increases from 350 μm to 650 μm for each combination, FIG. 3C depicts calculated back-reflection versus lens radius r and incident angle θ in the endoscope using an NCF length of 500 θm. The desired incident angle of 52.5° was indicated by a red dot in FIGS. 3D-3H. Chromatic focal shift is shown in FIG. 3D, focused spot size is shown in FIG. 3E, astigmatism ratio is shown in FIG. 3F, effective depth of focus (DOF) is shown in FIG. 3G, and working distance is shown in FIG. 3H which depicts calculated at different NCF lengths L and lens radii r when the incident angle is 52.5°, FIG. 3I depicts optimal design region compiled from the calculated results in FIGS. 3D-3H. The design adopted to fabricate the endoscope is indicated with a red dot, in accordance with some embodiments of the subject invention.

FIGS. 5A-5I depict OCT endoscope characterization, wherein FIG. 5A is an image of a rigid endoscope and zoomed-in view of its distal optics (inset). FIG. 5B is an image of a flexible endoscope and zoomed-in view of its distal optics (inset). FIG. 5C shows measured 3D profile of the liquid-shaped lens used in endoscope, FIG. 5D is an image of 1D surface profiles of lens extended by nonlinear least square fitting the measurements along four representative radial angles at 0°, 45°, 90°, and 135° (dashed lines in FIG. 5C). FIG. 5E shows representative surface roughness measured on the top curved surface of the lens (dashed circle in FIG. 5C). FIG. 5F shows representative surface roughness measured on the flat reflective surface of lens. FIG. 5G shows representative focused laser beam profile and focused laser spot (inset) measured out of a 0.6-mm protective glass capillary tube of the rigid endoscope. The x-axis represents the distance relative to the focal plane along the light-emitting direction, and 0 μm is the location of focal plane. The beam diameters in x and y directions are measured using an optical beam profiler, and the mean diameters are calculated using weighted equations provided by DataRay, i.e., w=0.83114×x+0.16886×y when x≥y, or w=0.16886×x+0.83114×y when x<y; w is the mean diameter, and x and y indicate the beam diameters in x and y directions, respectively. FIG. 4H depicts axial resolution measured along the imaging depth with a representative point spread function (inset). Here 0 μm in imaging depth is where the zero optical-delay position between the reference and sample arms is located. FIG. 5I shows back-reflected spectra obtained by moving a mirror along the light-emitting direction and measured out of the protective sheath of endoscope.

Here 0 μm indicates the position of focal plane, in accordance with some embodiments of the subject invention.

Figure 6A:
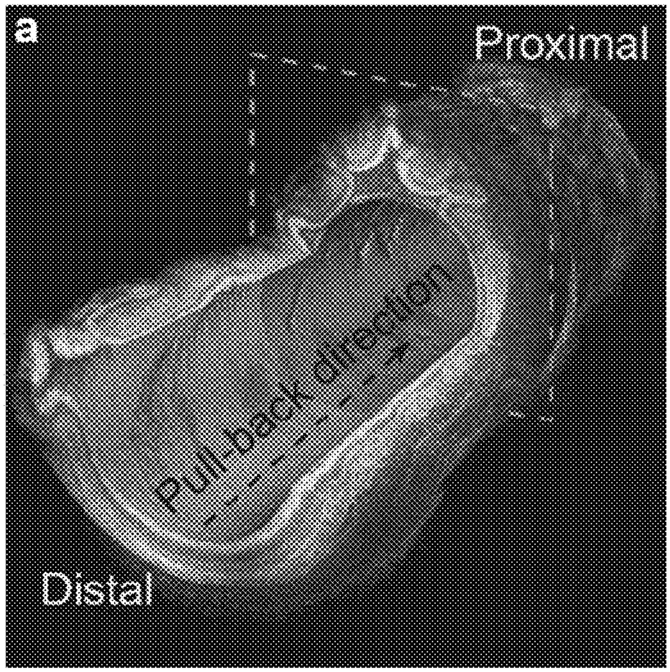
Figure 6B:
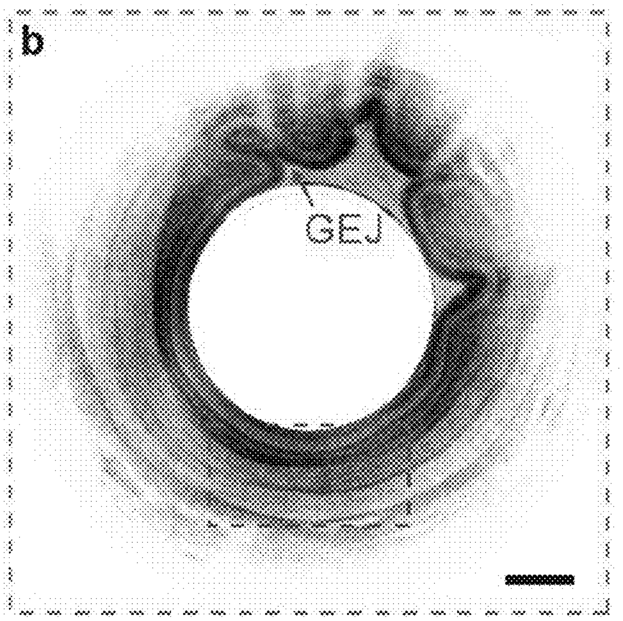
Figure 6C:
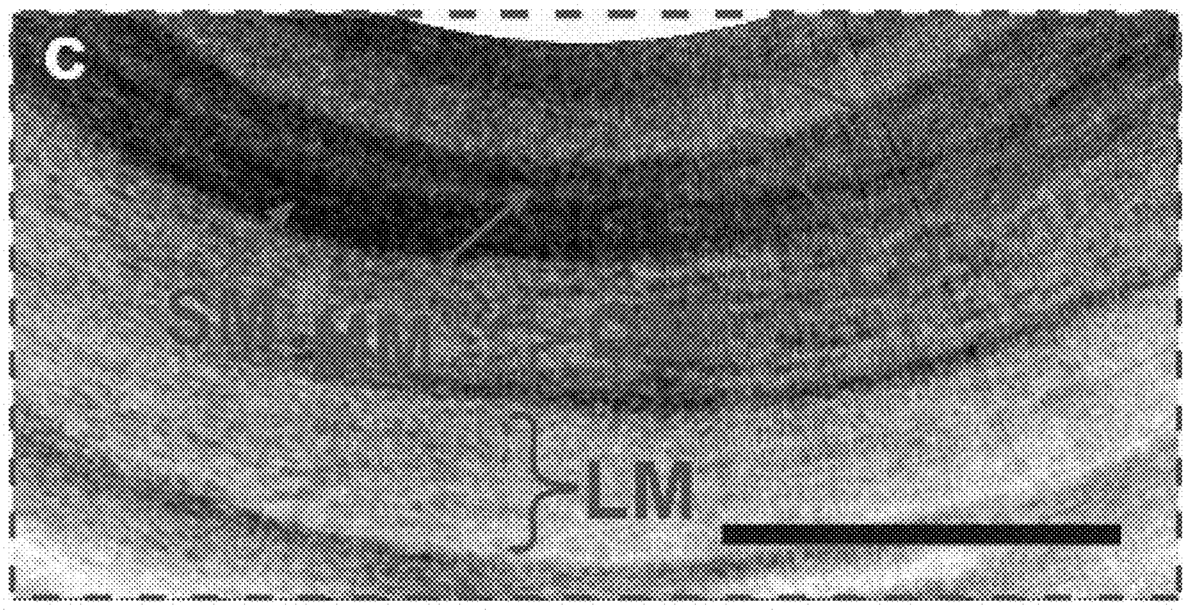
Figure 6D:
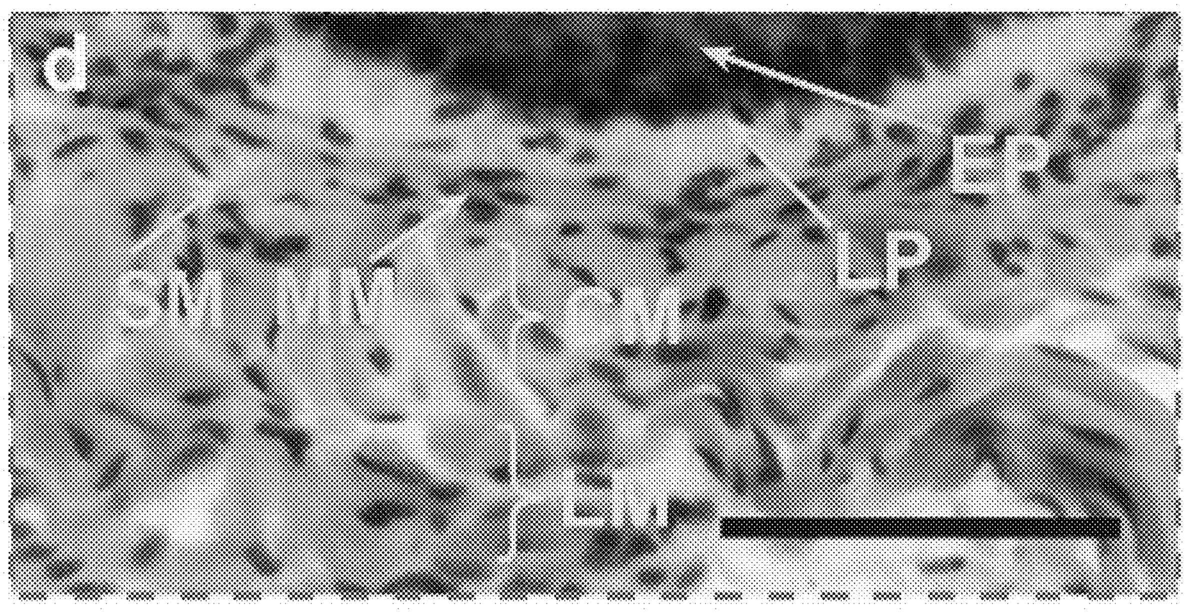

FIGS. 6A-6D show imaging rat esophagus using flexible endoscope, wherein FIG. 6A shows cut-way view of a reconstructed 3D OCT image of a 36-mm-long rat esophagus adjacent to GEJ. FIG. 6B shows representative 2D OCT image corresponding to the cross-section boxed with green dashed lines in FIG. 6A, FIG. 6C shows 3× close-up view of the region labeled with red dashed box in FIG. 6B, FIG. 6D shows correlated hematoxylin and eosin (H&E) histology. GEJ: gastroesophageal junction, EP: stratified squamous epithelium, LP: lamina propria, MM: muscularis mucosae, SM: submucosa, CM: circular muscle, LM: longitudinal muscle. Scale bars are 250 μm, in accordance with some embodiments of the subject invention.

Figure 7A:
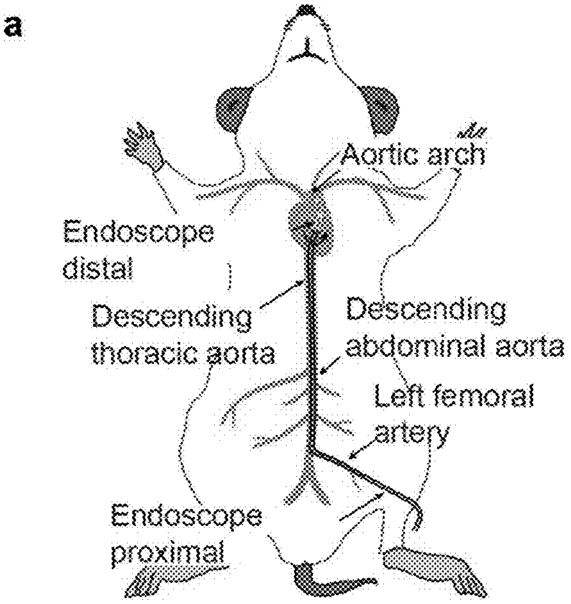
Figure 7B:
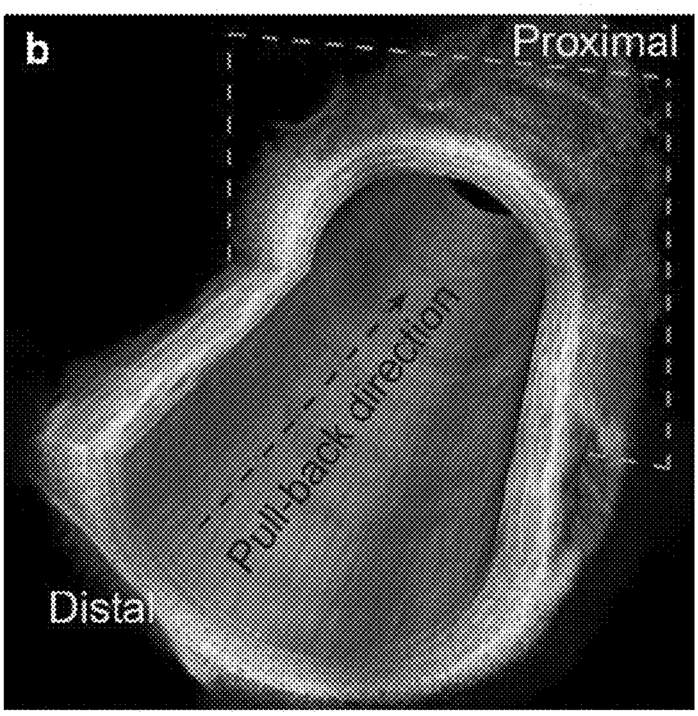
Figure 7C:
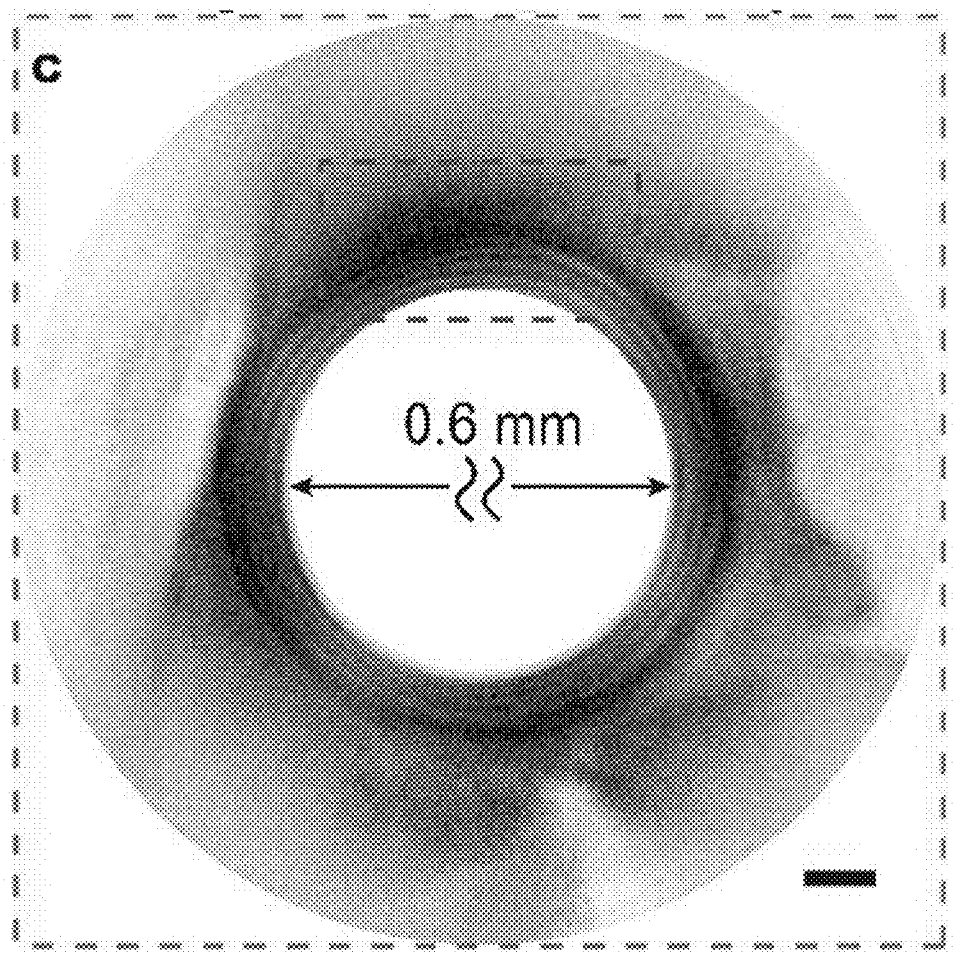
Figure 7D:
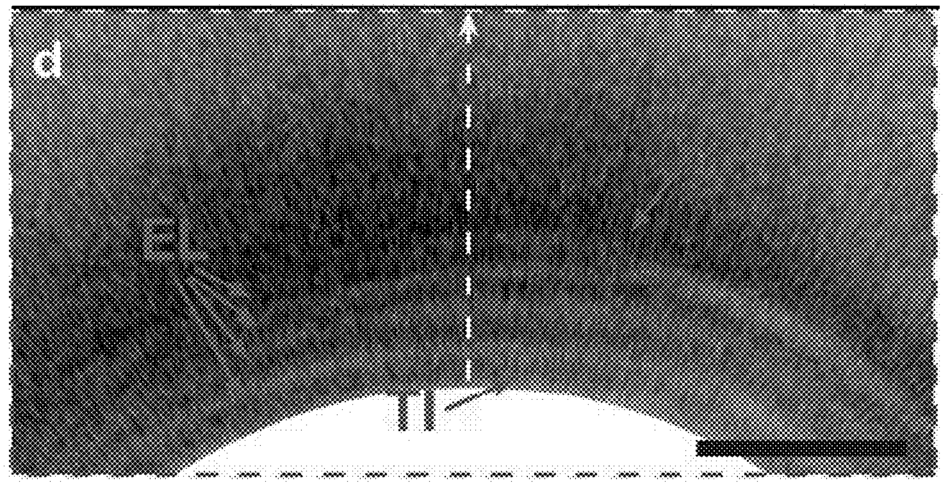
Figure 7E:
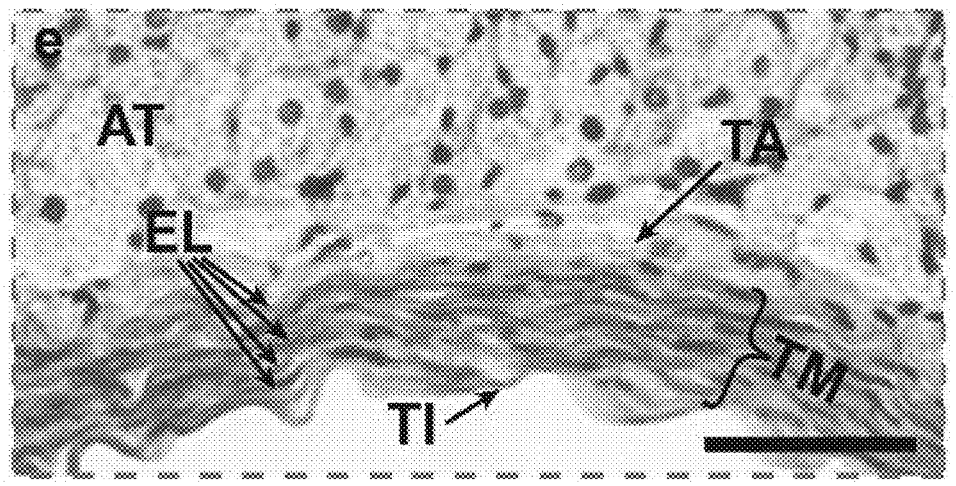
Figure 7F:
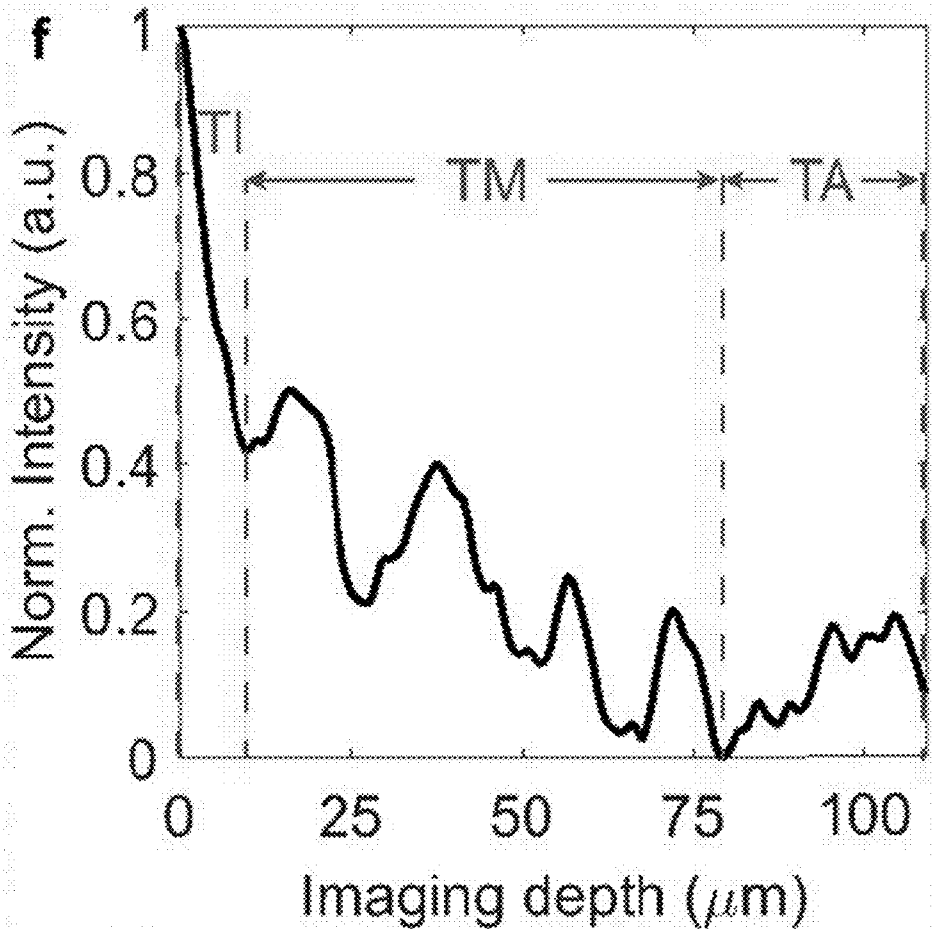
Figure 7G:
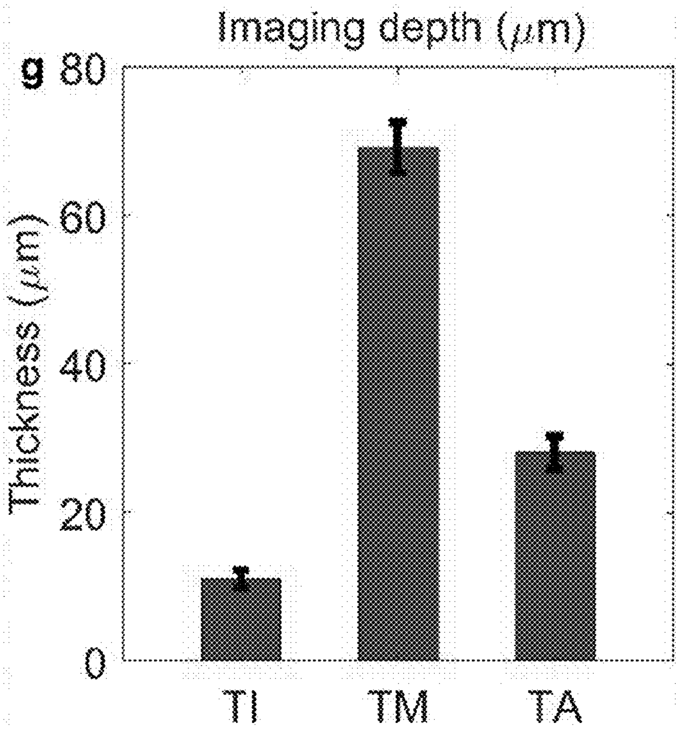

FIGS. 7A-7G show in situ imaging of mouse aorta with flexible endoscope, wherein FIG. 7A shows that a flexible endoscope is deployed from the left femoral artery to the aortic arch in the mouse, FIG. 7B shows cut-way view of a reconstructed 3D OCT image of a 14.6-mm-long mouse descending thoracic aorta, FIG. 7C shows representative OCT cross section indicated with a green dashed box in FIG. 7B, FIGS. 7D and 7E show 3× close-up view of the region boxed with red dashed lines in FIG. 7C and its correlated hematoxylin and eosin (H&E) histology. The white arrow points to the deep tissue. FIGS. 7F and 7G show example quantification of each fine tissue layer's thickness (distance between red dashed lines) of mouse aorta along an A-line depth (the white arrow in FIG. 7D) as shown in FIG. 7F. FIG. 7G shows that the thickness and its standard deviation of each aorta layer were measured using 40 A-lines from 10 representative OCT cross-sections, TI: tunica intima, TM: tunica media, TA: tunica adventitia, EL: elastic lamellae, AT: adipose tissue, scale bars are 100 μm, in accordance with some embodiments of the subject invention.

Figure 8A:
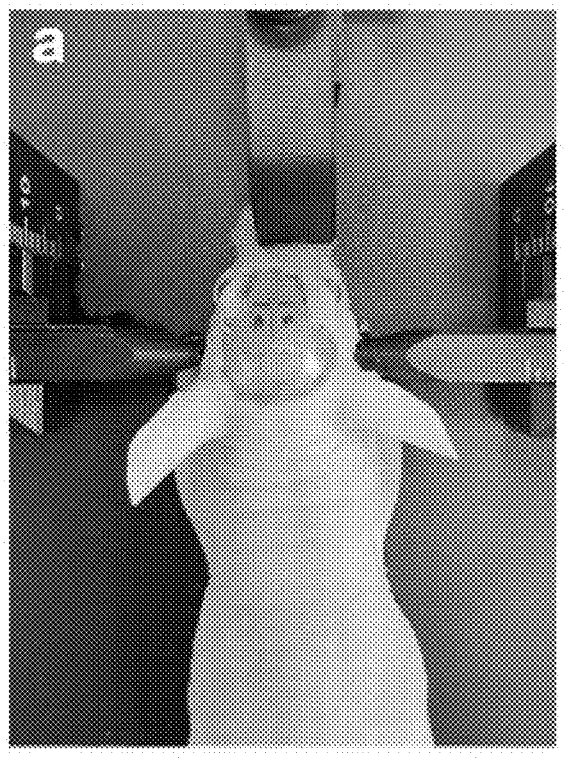
Figure 8B:
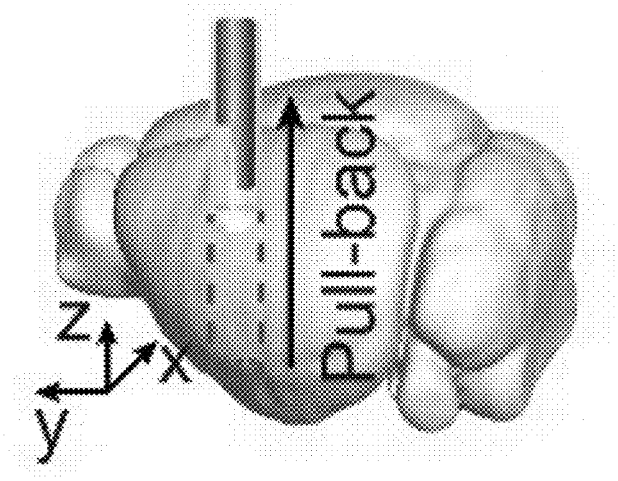
Figure 8C:
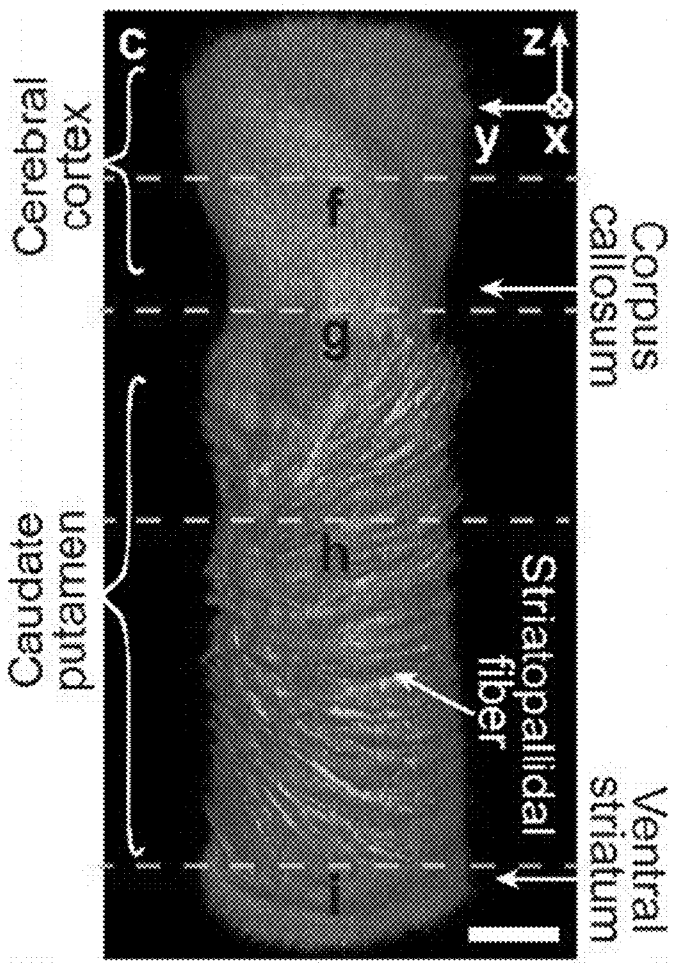
Figure 8D:
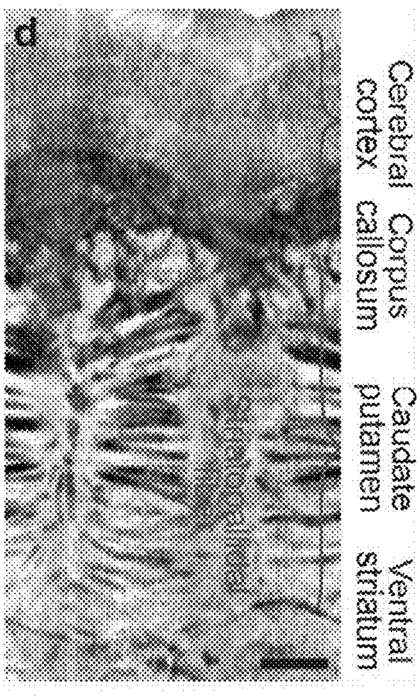
Figure 8E:
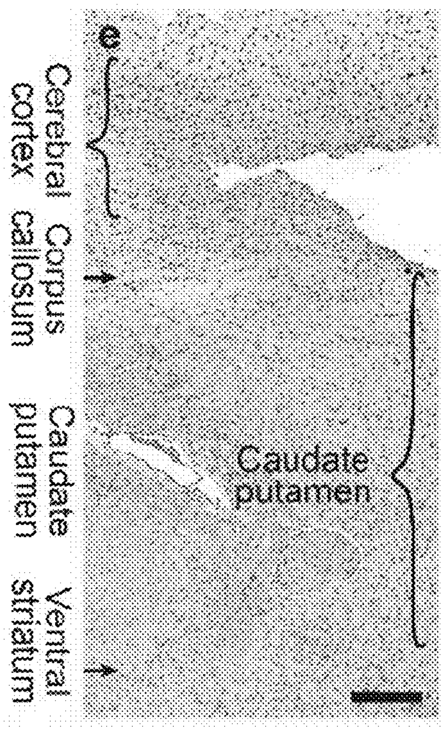
Figure 8F:
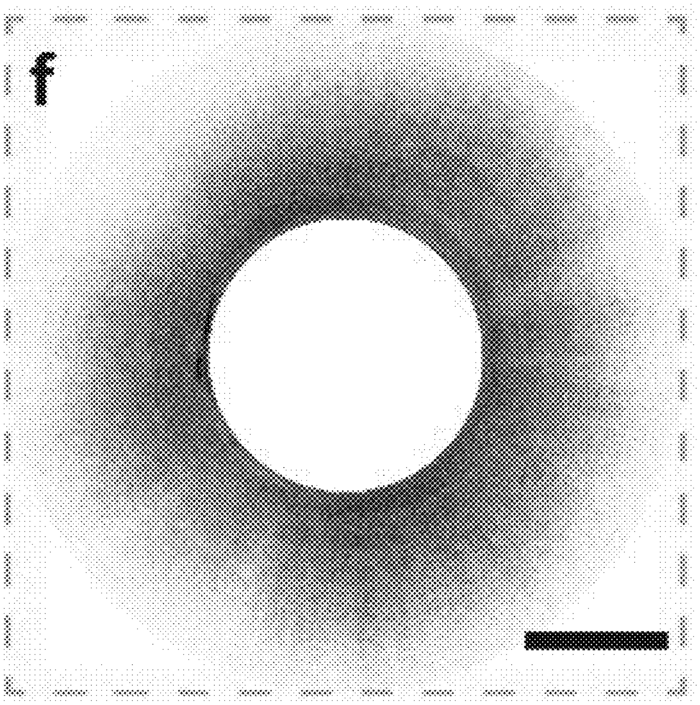
Figure 8G:
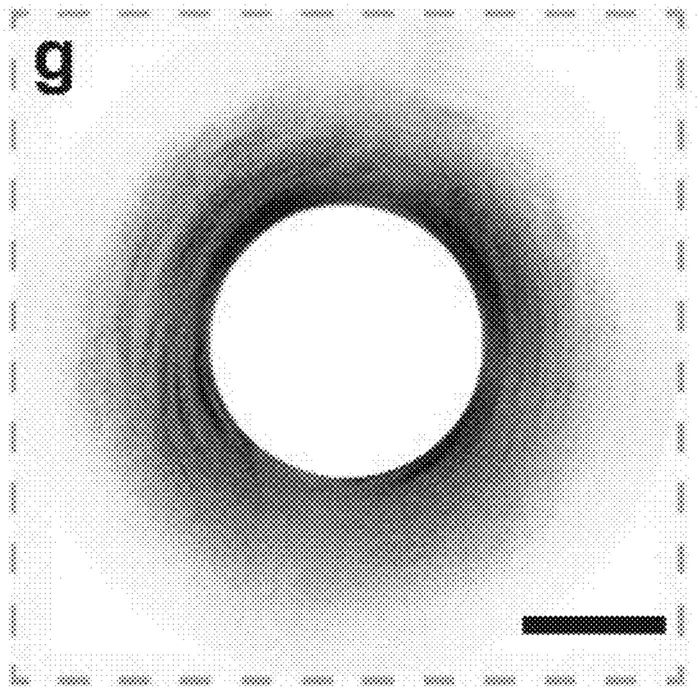
Figure 8H:
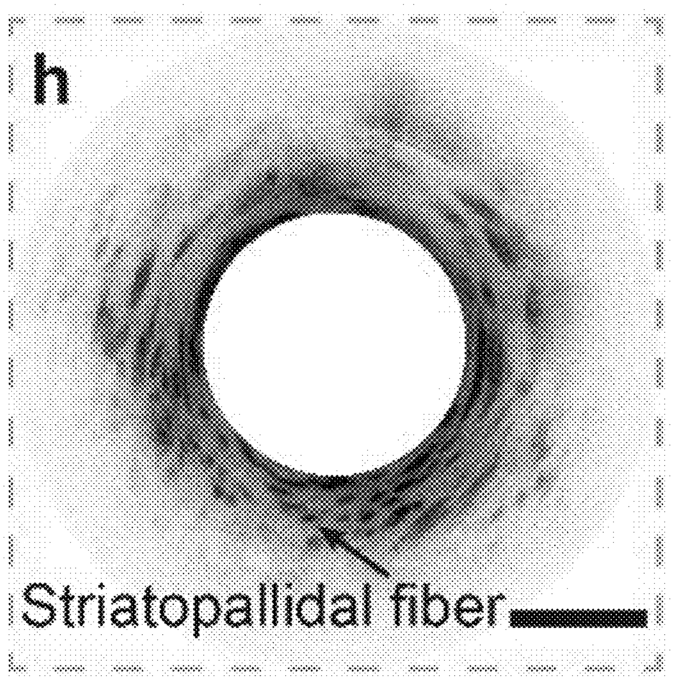
Figure 8I:
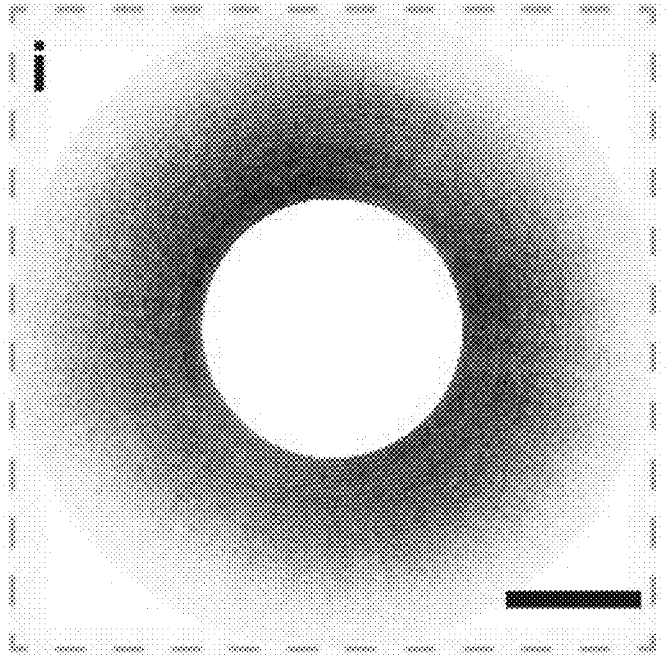

FIGS. 8A-8I show in vivo imaging of mouse deep brain with rigid endoscope, wherein FIG. 8A shows the preparation of mouse brain for imaging with the scalp incised and two burr holes (about 1 mm in diameter) on skull. FIG. 8B is schematic of endoscope imaging in mouse deep brain, FIG. 8C shows reconstructed volumetric mouse brain image of 5-mm depth, FIG. 8D shows en face projection view of the unfolded cylindrical OCT volume shown in FIG. 8C. FIG. 8E shows hematoxylin and eosin (H&E) histology micrograph of brain sample correlated to FIG. 8C and FIG. 8D. FIGS. 8F-8I show representative cross-sectional images of different mouse brain structures, including cerebral cortex (FIG. 8F), corpus callosum (FIG. 8G), caudate putamen (FIG. 8H), and ventral striatum (FIG. 8I), corresponding to dashed lines in FIG. 8C, scale bars are 500 μm, in accordance with some embodiments of the subject invention.

Figure 9A:
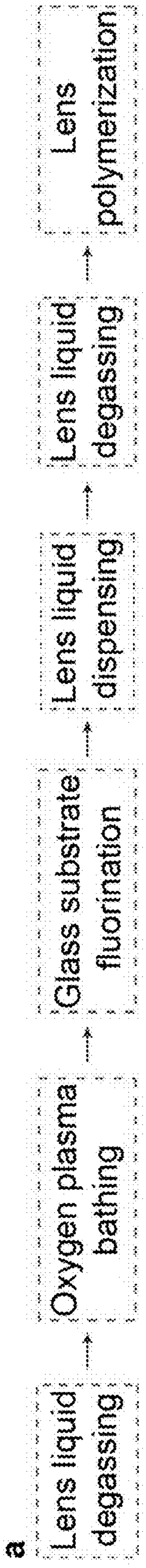
Figure 9B:
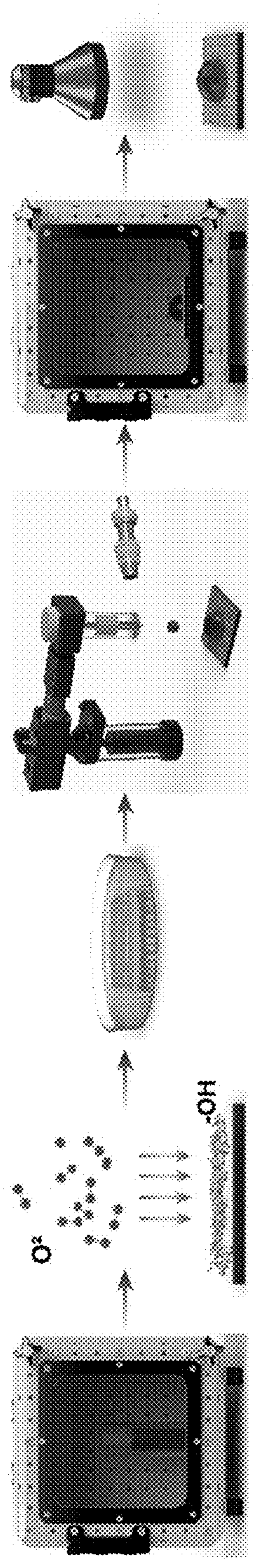
Figure 10A:
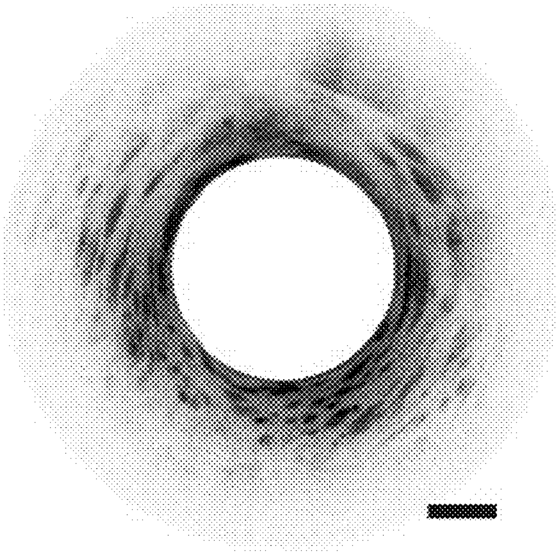
Figure 10B:
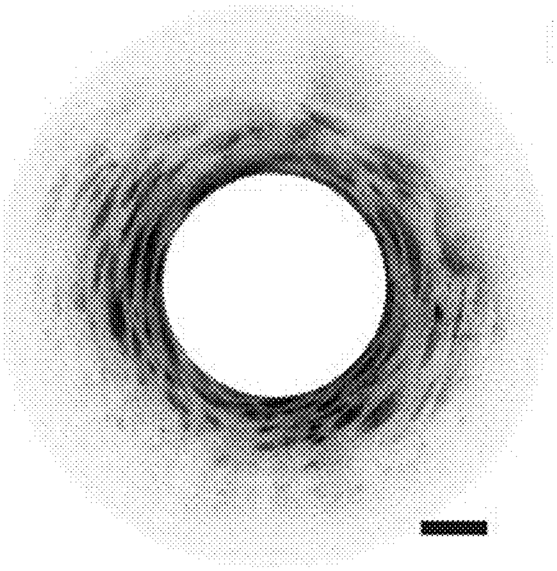
Figure 10C:
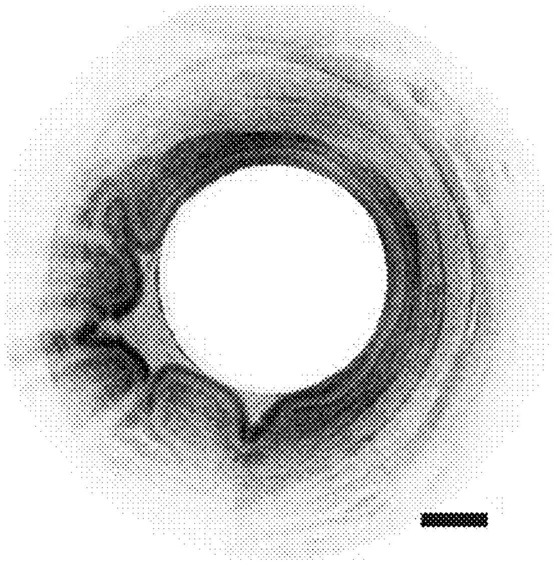
Figure 10D:
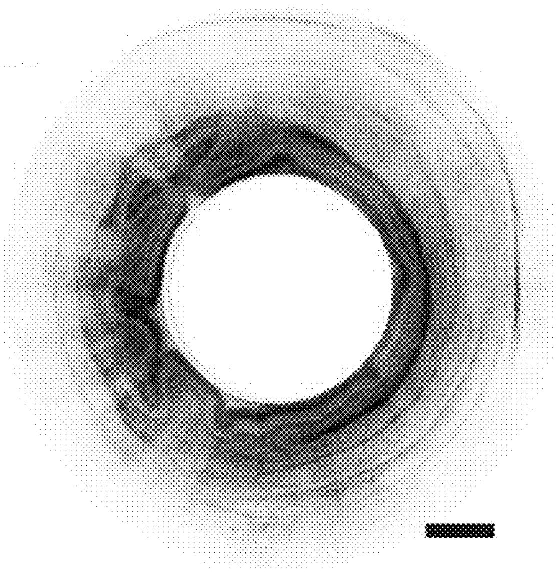
Figure 10E:
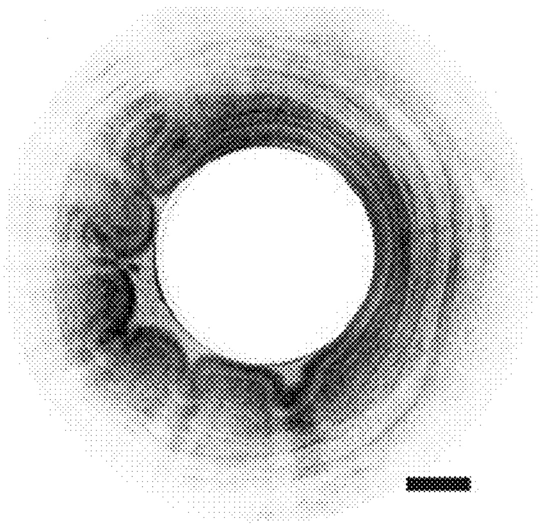

FIGS. 9A-9B show procedures for fabricating liquid-shaped lens, wherein FIG. 9A shows the flow chart of lens fabrication, wherein FIG. 9B shows the procedures for fabricating the liquid-shaped lens, different colors of the glass substrate indicate the modification process of the glass surface property: yellow indicates that the hydroxy (—OH) was exposed on the glass surface during oxygen plasma cleaning; green indicates that the fluoride was reacting with the hydroxy; purple indicates that the hydroxy was bonded entirely with the fluoride and the glass substrate was fully fluorinated, in accordance with some embodiments of the subject invention.

FIGS. 10A-10E show imaging results of simultaneously fabricated endoscopes, wherein the first two images (FIGS. 10A and 10B) show 2D cross-sectional images of mouse brain obtained from #1 and #2 rigid endoscopes, respectively. The last three images (FIGS. 10C, 10D, and 10E) show the cross-sectional images of rat esophagus obtained from #3, #4, and #5 flexible endoscopes, respectively. The imaging results demonstrate the comparable performance of the simultaneously fabricated endoscopes. All scale bars are 250 μm, in accordance with some embodiments of the subject invention.

Figure 11:
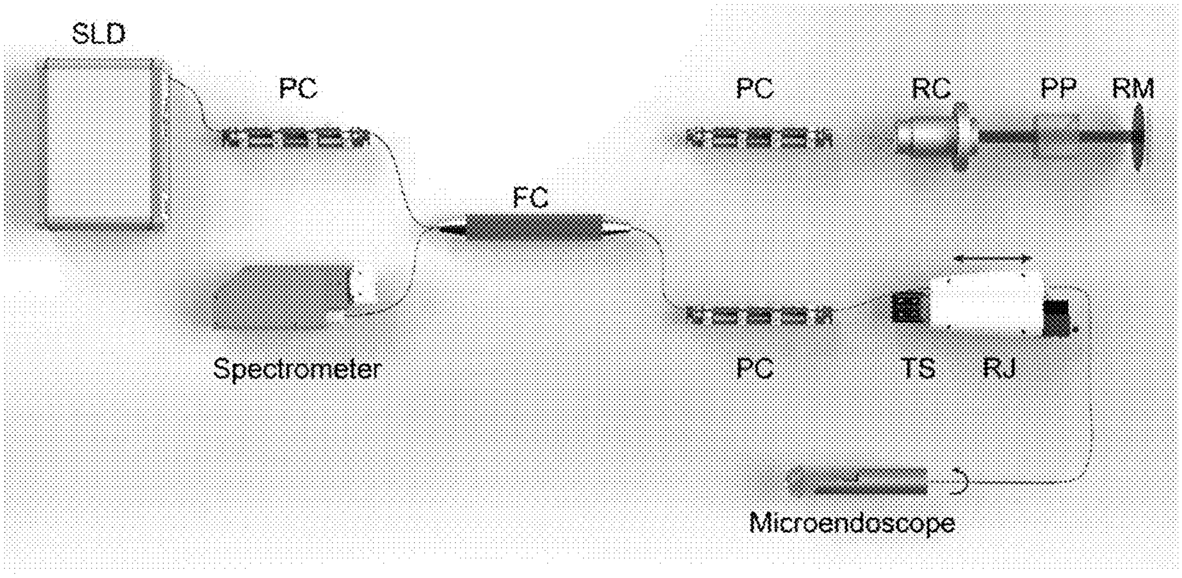

FIG. 11 shows schematic of the endoscopic spectral-domain OCT (SD-OCT) system, SLD: superluminescent diode, PC: polarization controller, FC: fiber coupler, RC: reflective collimator, PP: prism pairs, RM: reflective mirror, TS: translational stage, RJ: rotary joint, in accordance with some embodiments of the subject invention.

Figure 12:
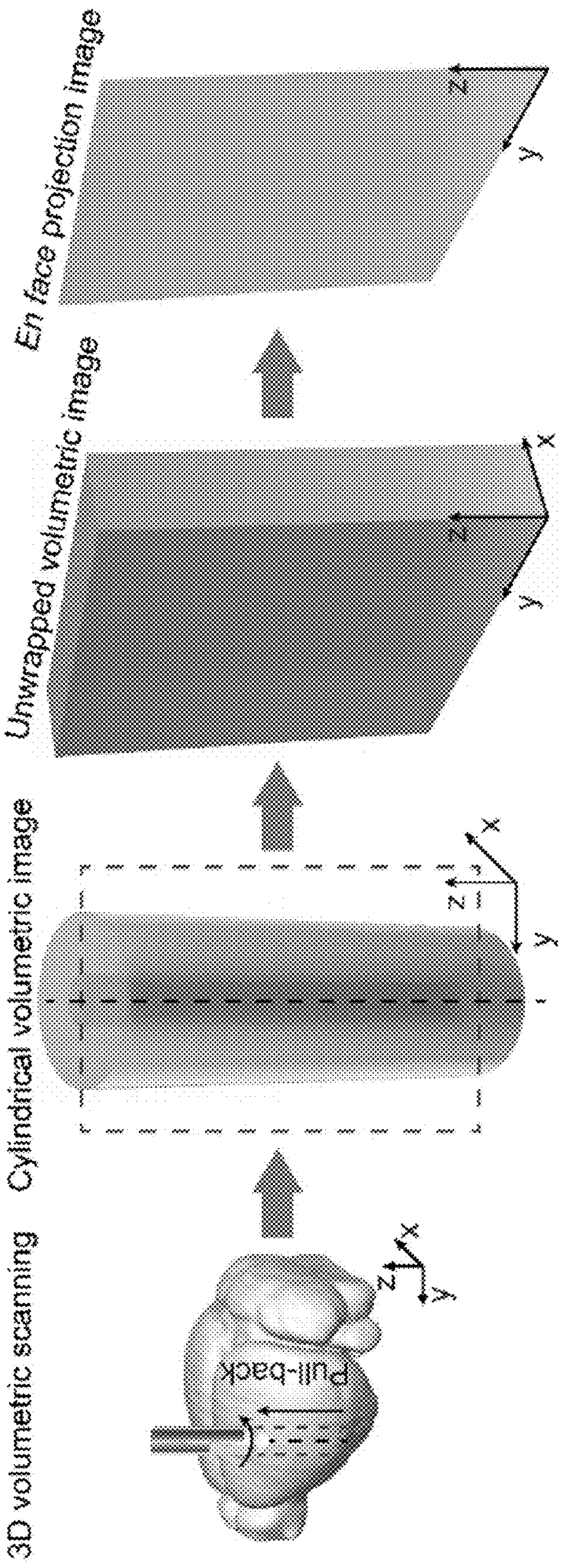
Figure 13A:
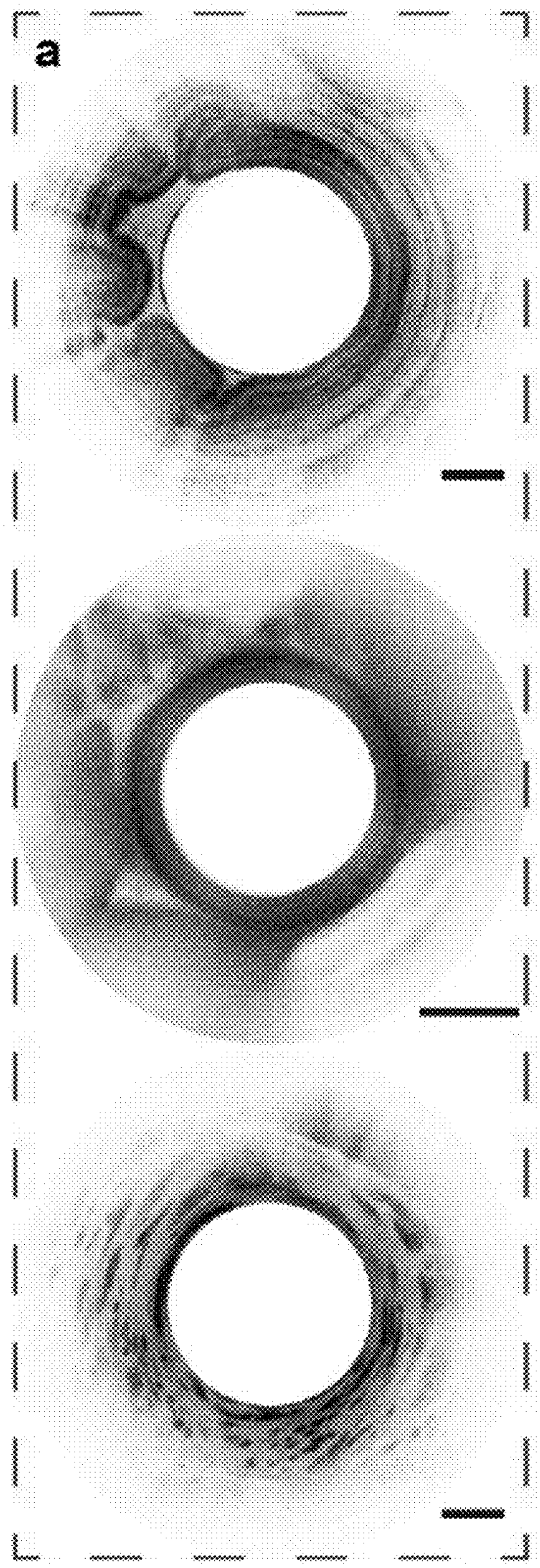
Figure 13B:
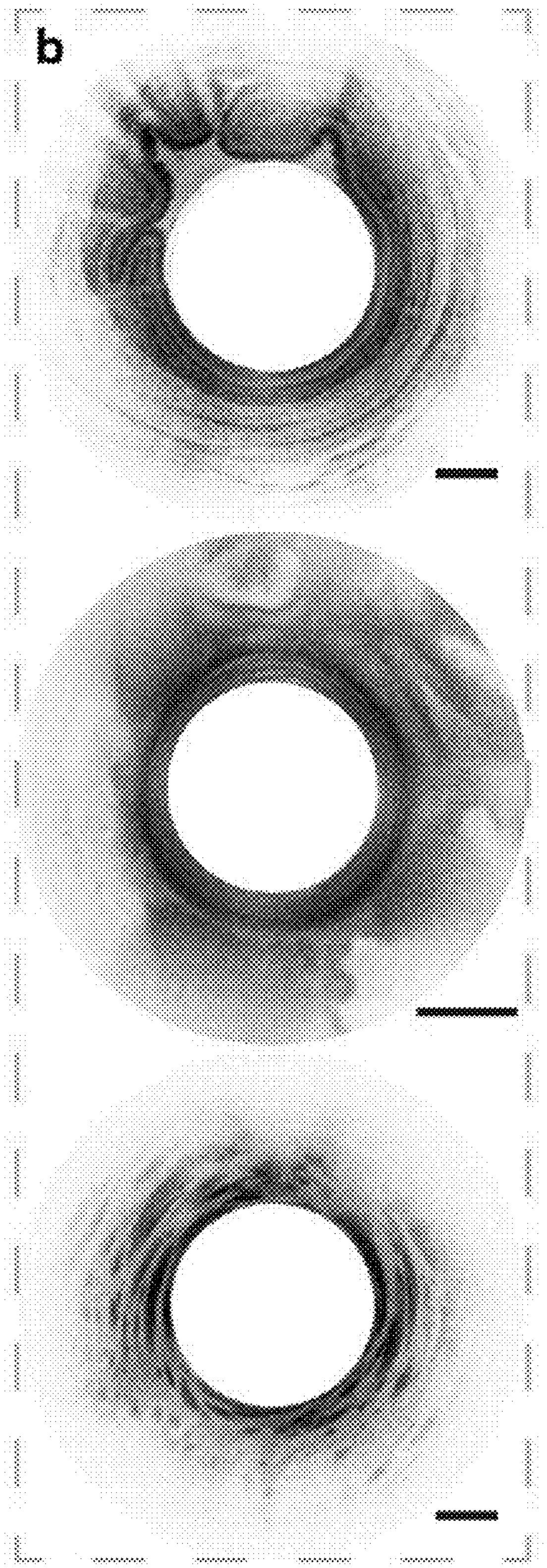
Figure 13C:
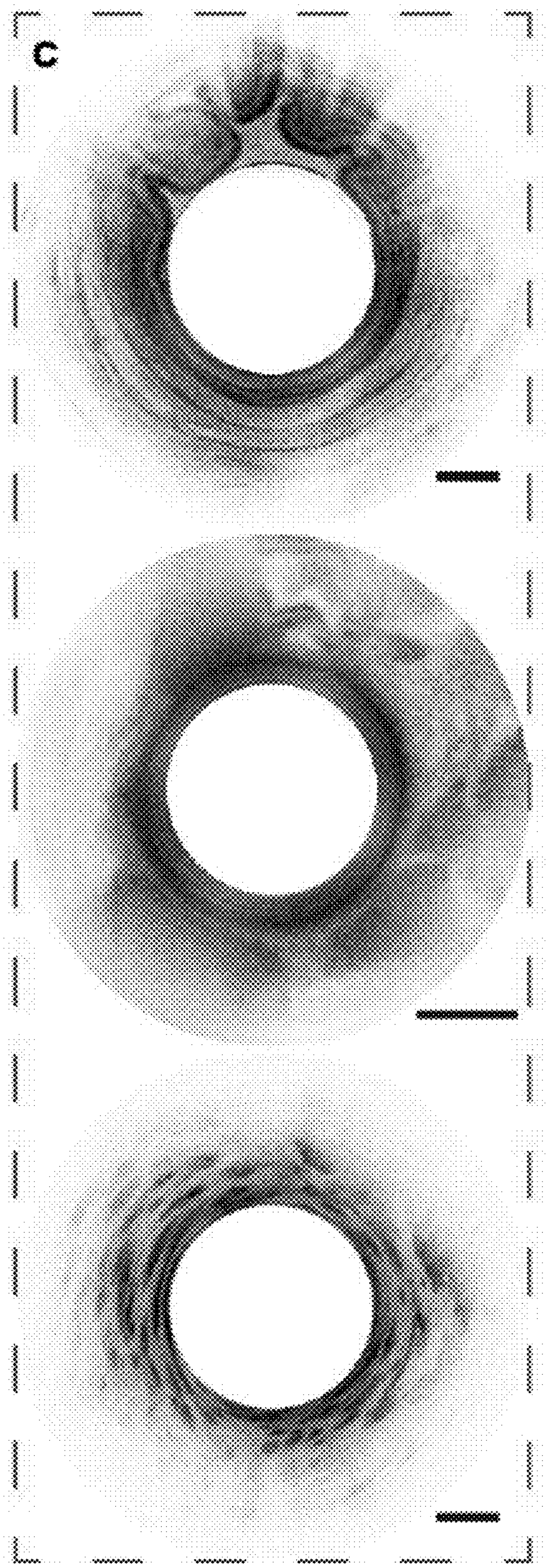
Figure 13D:
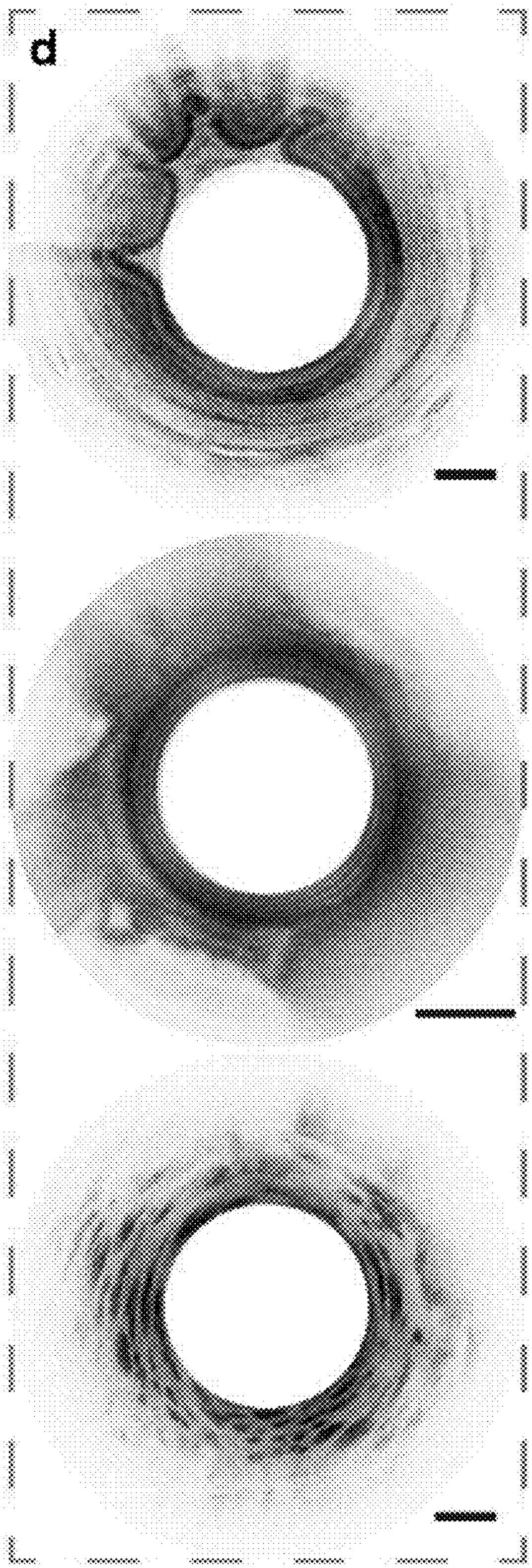

FIG. 12 illustrates OCT scanning in mouse deep brain and the enface projection procedures, in accordance with some embodiments of the subject invention.

FIGS. 13A-13D show long-term stability on imaging performance of the fabricated endoscopes, wherein the 2D cross-sectional images of the rat esophagus, mouse aorta, and mouse deep brain (from top to bottom) obtained when the endoscopes were fabricated at 1 month (FIG. 13A), 3 months (FIG. 13B), 6 months (FIG. 13C), and 12 months (FIG. 13D), the comparable imaging results demonstrate the long-term stability of the endoscopes, all scale bars are 250 μm, in accordance with some embodiments of the subject invention.

Figure 14:
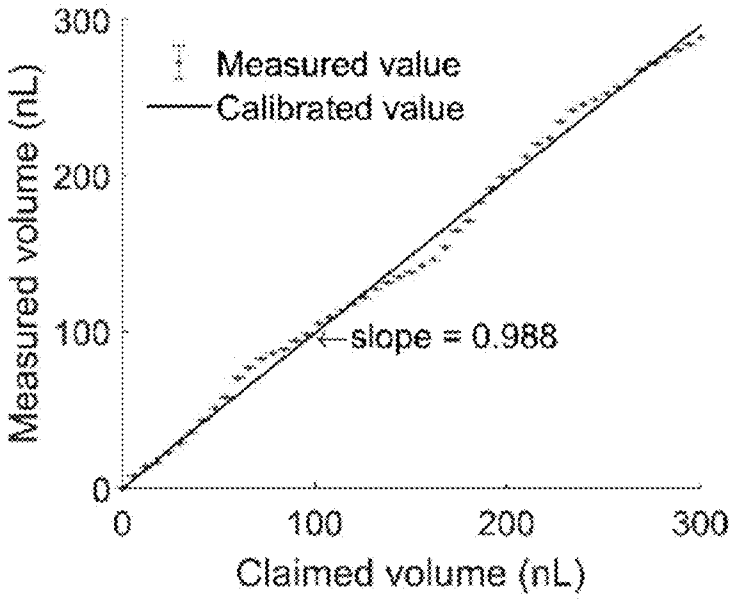

FIG. 14 shows calibration of dispensed liquid volume, wherein a series of liquid volumes claimed by the dispenser was dispensed on the glass substrate to form the liquid lens, and the volume was measured (with a measurement accuracy of ±0.05 nL), the slope of the fitted line is about 0.988 and is used to calibrate the claimed dispensed volume, in accordance with some embodiments of the subject invention.

Figure 15:
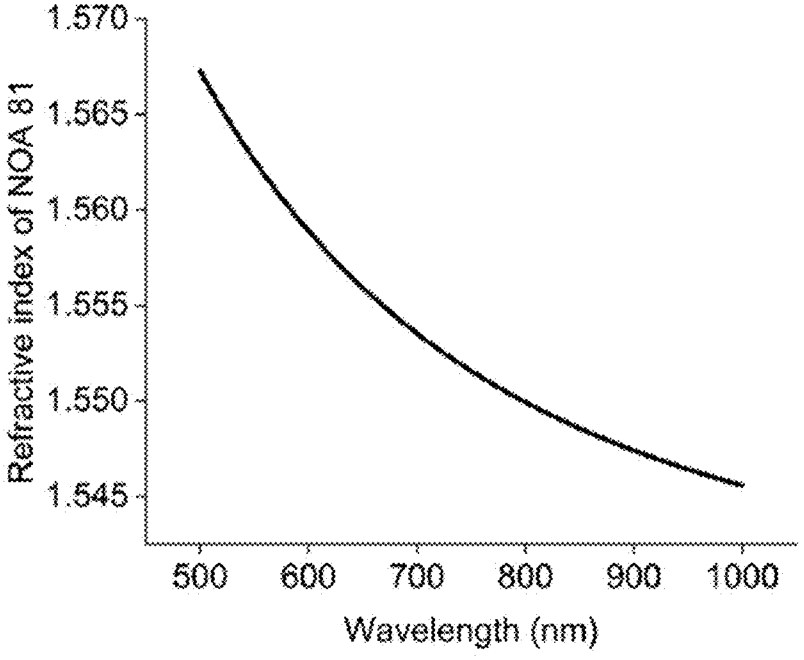

FIG. 15 shows refractive index profile of NOA 81 under room temperature, in accordance with some embodiments of the subject invention.

Figure 16:
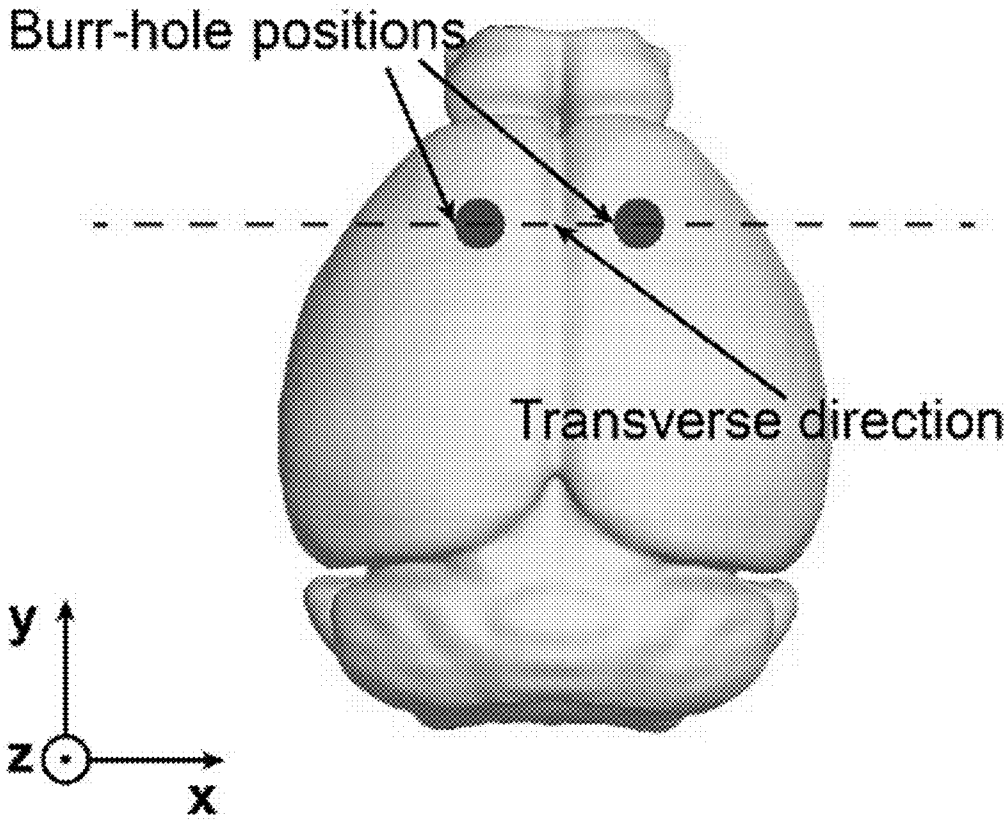

FIG. 16 is schematic of mouse brain handling for histology, wherein the red dots indicate the burr-hole positions where the glass capillary tubes were inserted. The blue dashed line indicates the transverse direction for brain tissue dissection (the cross-section parallel to the x-z plane), in accordance with some embodiments of the subject invention.

DETAILED DESCRIPTION

Embodiments of the subject invention are directed to a liquid shaping technique for the rapid and scalable fabrication of high-performance OCT endoscopes.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention pertains. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

When the term "about" is used herein, in conjunction with a numerical value, it is understood that the value can be in a range of 90% of the value to 110% of the value, i.e. the value can be +/−10% of the stated value. For example, "about 1 kg" means from 0.90 kg to 1.1 kg.

The present invention relates to a liquid shaping-based method and system for the scalable fabrication of disposable OCT endoscopes. The OCT endoscope and fabrication methods using liquid shaping techniques can be further understood by referring to FIGS. 1-16, which are described in further detail below. It is understood that the following examples depict exemplary endoscopes and fabrication methods and that variations can be realized without departing from the inventive concepts herein.

I. Overview

Figure 1A:
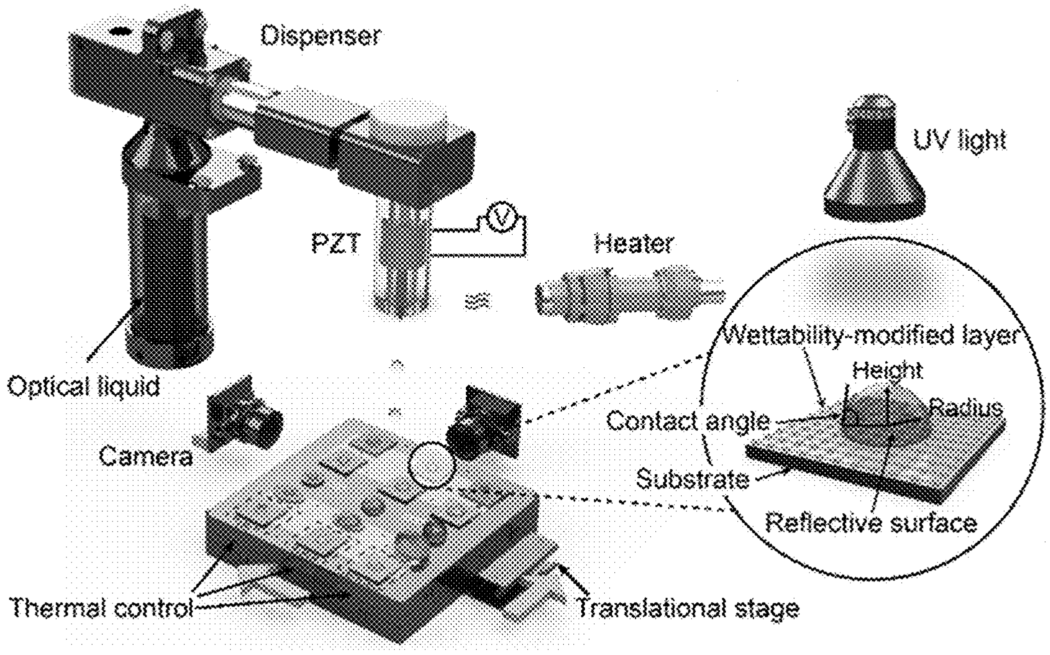
Figure 1B:
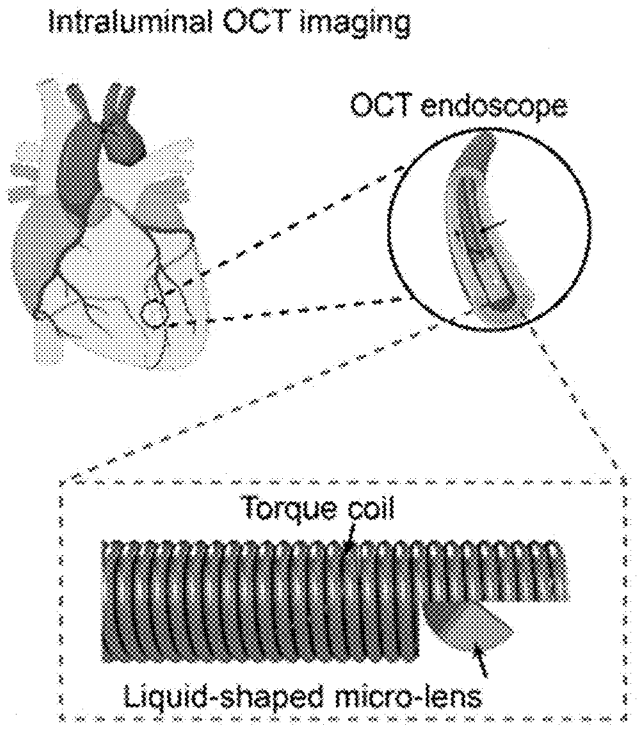
Figure 1C:
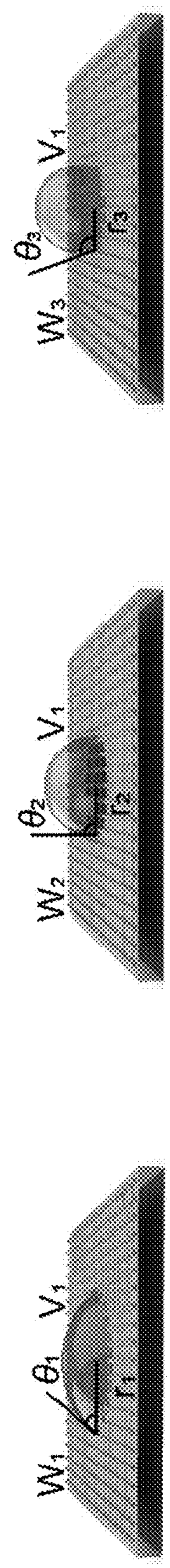
Figure 1D:
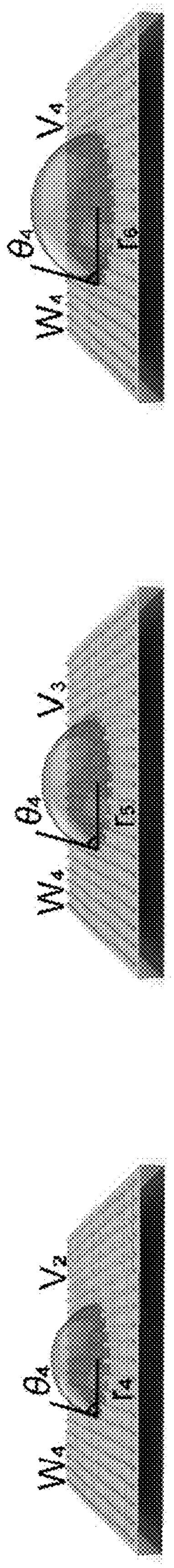

In one aspect, freeform lenses can be fabricated by manipulating the minimum energy state of curable optical liquid droplets on a wettability-modified substrate and used as focusing optics in OCT endoscopes for volumetric optical biopsy in complex luminal organs, as shown in FIGS. 1A-1B. Fabrication can entail using a liquid dispenser to dispense precisely controlled droplets on a substrate and controlling thermal conditions to form the liquid lens, as shown in FIGS. 1C-1G. In some embodiments, a piezoelectrically actuated dispenser was used to precisely control the volume of the optical liquid droplet (for example, NOA 81, Norland Product Inc. or any suitable liquid). A thermal control was employed by heating the dispenser nozzle with heater, to approximately 75° C. to reduce the liquid viscosity from 300 to 30 cps, facilitating easy dispensing of the optical liquid.

Referring to FIGS. 1A-1G, freefonm lenses can be fabricated by manipulating the minimum energy state of curable optical liquid droplets on a wettability-modified substrate (FIG. 1A) and used as focusing optics in OCT endoscope for volumetric optical biopsy in complex luminal organs (see FIG. 1B). Herein, a piezoelectrically actuated dispenser will be developed to precisely control the volume of the optical liquid droplet at accuracy of 0.1 nanoliter. Thermal control will be employed to heat up the dispenser nozzle to reduce the liquid viscosity, facilitating easy dispensing of the optical liquid to the substrate. The liquid temperature on substrate will be precisely controlled to adjust the liquid viscosity and thus the surface shape and size. The substrate will be placed on a two-dimensional translational stage to enable the mass production of freeform lens of custom shape and size in 10 minutes (see FIG. 1A). The polymerization of freeform lens will be performed using an ultraviolet (UV) lamp. This approach enables the production of lenses of various shapes and sizes within tens of minutes by controlling a substrate's wettability (or surface energy, see FIG. 1C), the liquid volume (FIG. 1D), and physical boundaries (i.e., circular or elliptical, FIGS. 1E and 1F). In addition to the passive method, the lens shape can also be manipulated by the active thermal control of the optical liquid on a substrate (see FIG. 1G). Furthermore, the liquid-shaped lens provides a reflective surface with sub-nanometer surface roughness (see FIG. 1A), eliminating the additional angle-polishing process required in conventional methods based on GRIN fiber and fiber ball lens.

Referring to FIGS. 2A-2G, the versatility of this technique was validated through the continuous adjustment of the contact angle of approximately 50 nL of optical liquid on a glass substrate (which has no physical boundary for the liquid) from about 50° to 110° at an angle precision of about 0.5°. This was achieved by altering the substrate's wettability using a fluorination-based surface wettability modification method. Once the desired contact angle (such as 90°) of the lens was confirmed, the lens radius ranging from 120 to 720 μm was achieved at a resolution of approximately 1 μm by precisely controlling the droplet volume with a precision of approximately 0.1 nL (see FIG. 2B), thereby verifying the scale-invariant nature of the liquid shaping technique. The measured radii (and heights) of lenses made of different liquid volumes on glass substrates with defined wettability and contact angles closely aligned with the theoretically calculated radii (see FIG. 2C). This indicates the satisfactory controllability of the liquid shaping technique in creating spherical and aspherical lenses of predefined shapes and sizes on substrates without physical boundaries.

Figure 1E:
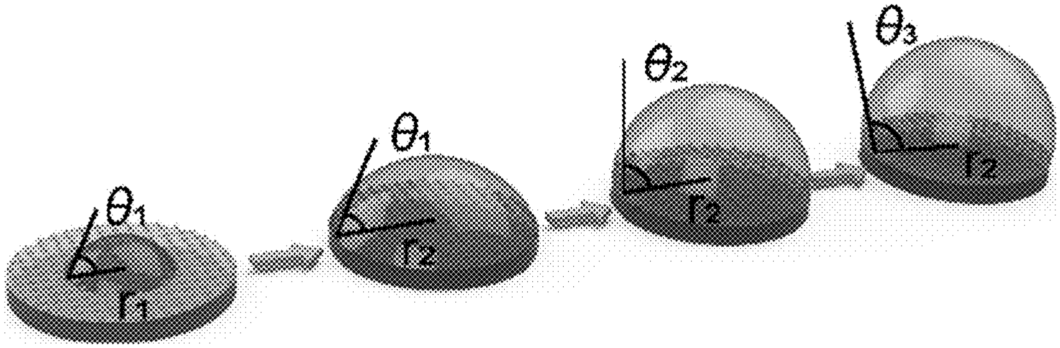
Figure 1F:
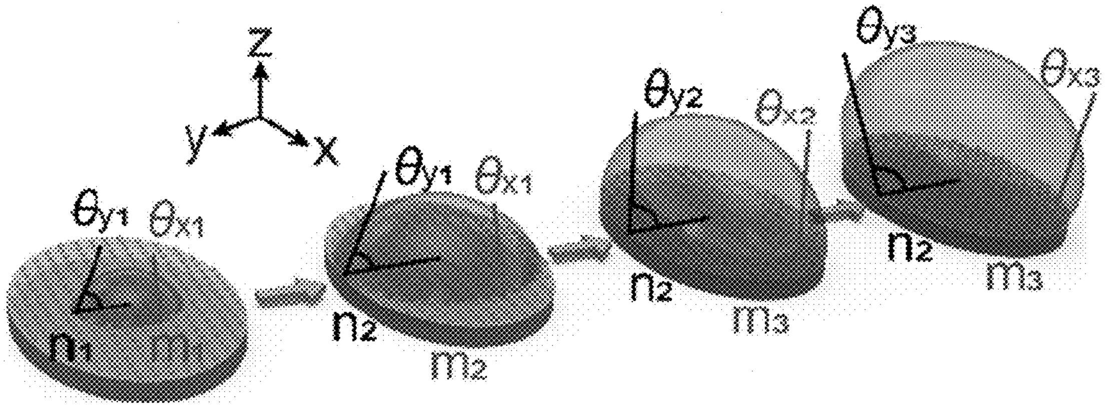
Figure 1G:
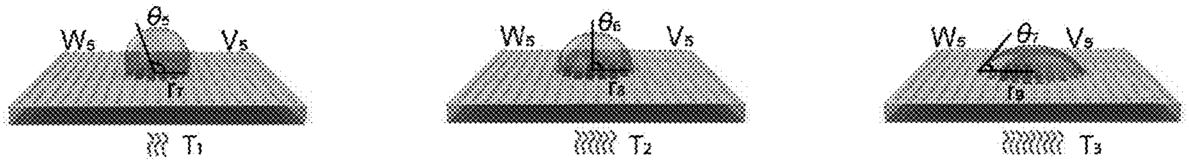
Figure 2A:
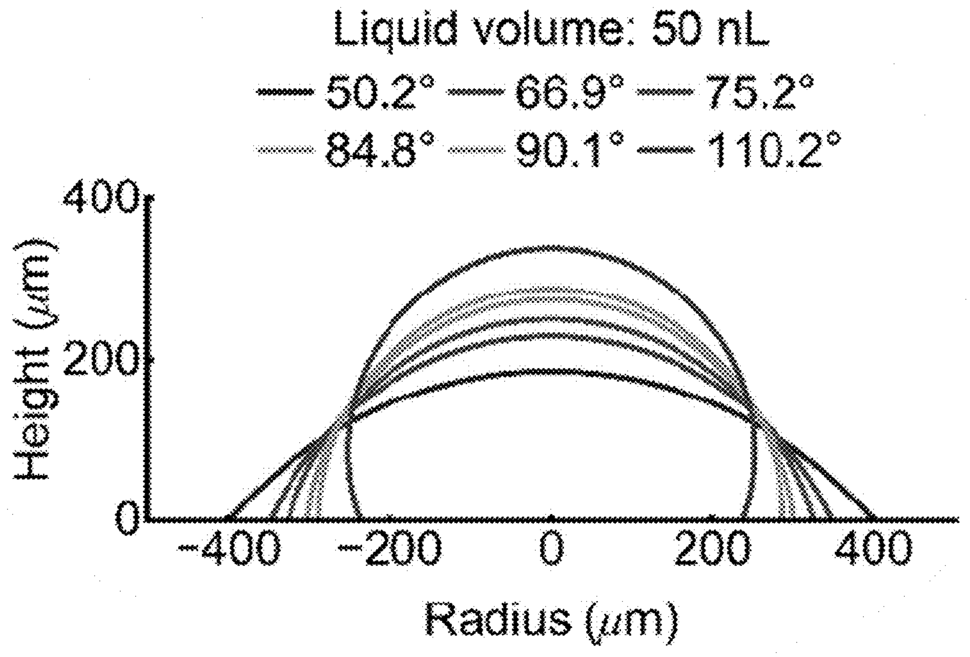
Figure 2B:
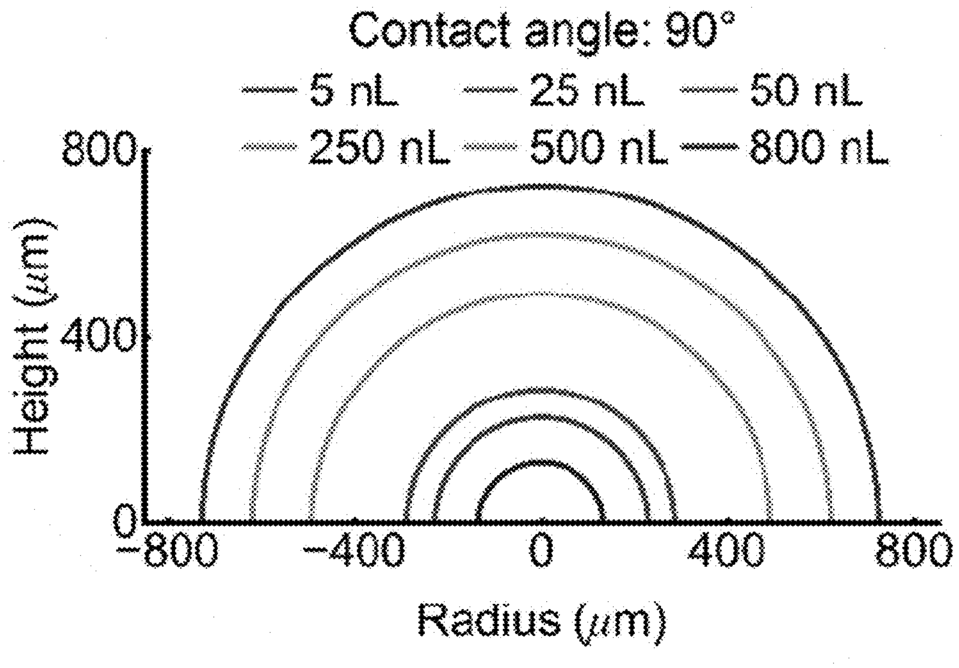
Figure 2C:
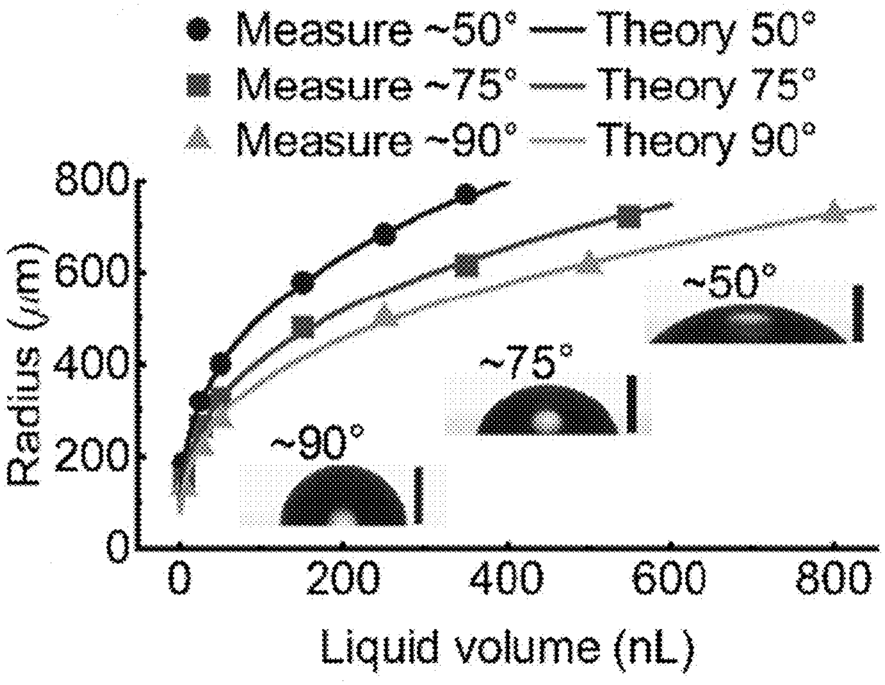
Figure 2D:
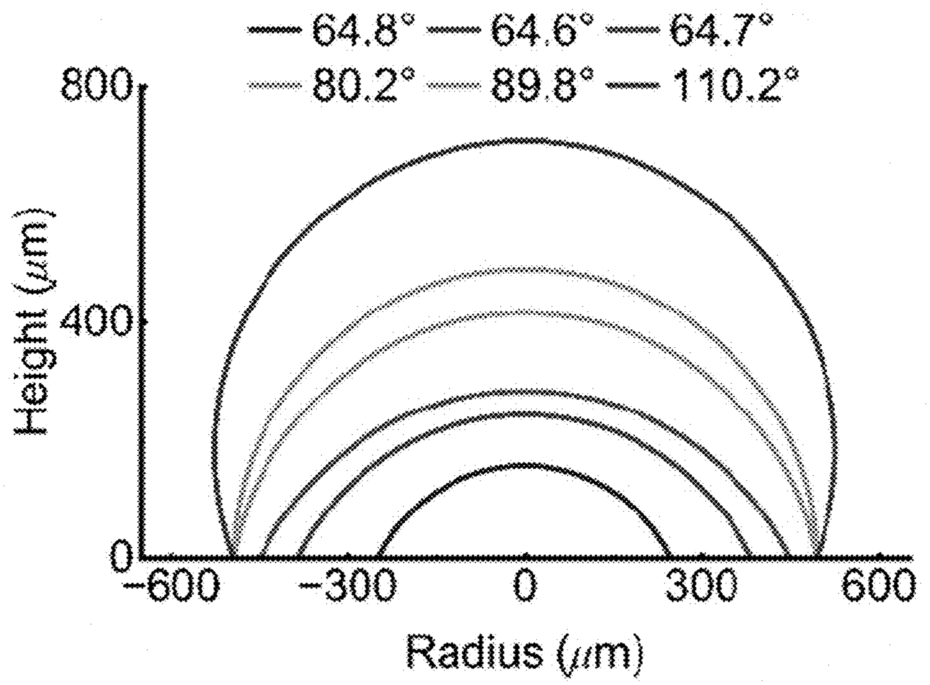
Figure 2E:
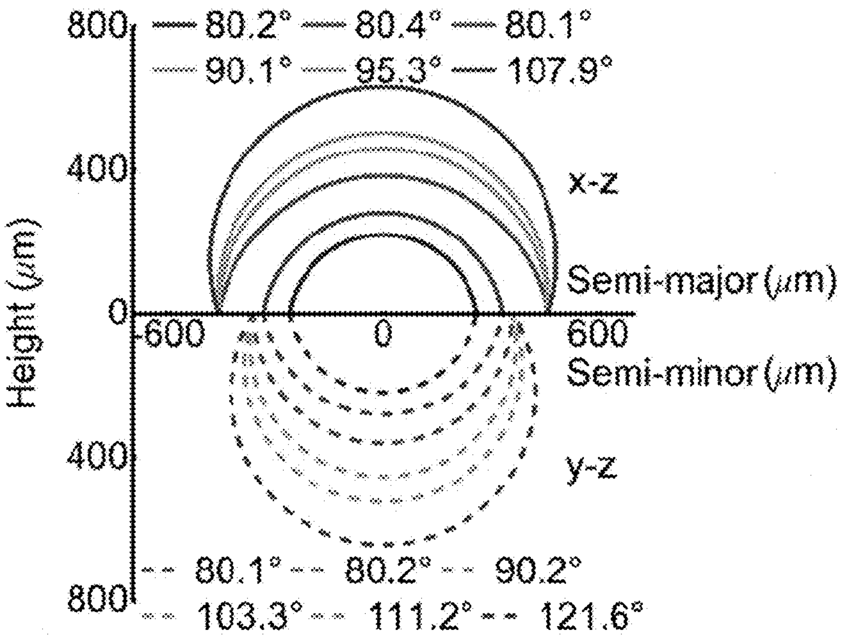
Figure 2F:
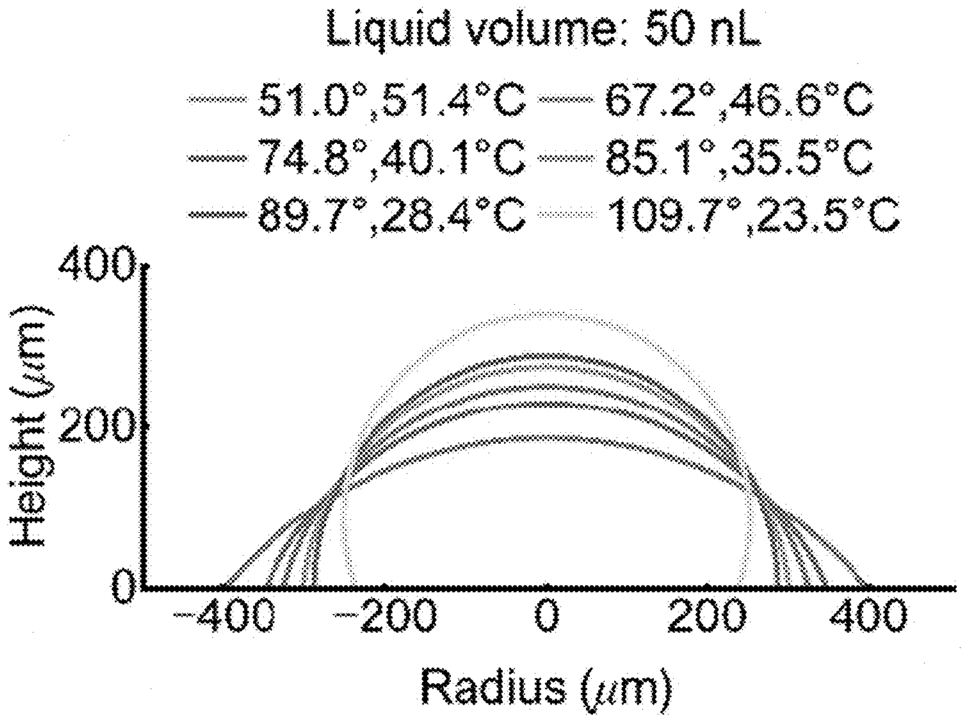
Figure 2G:
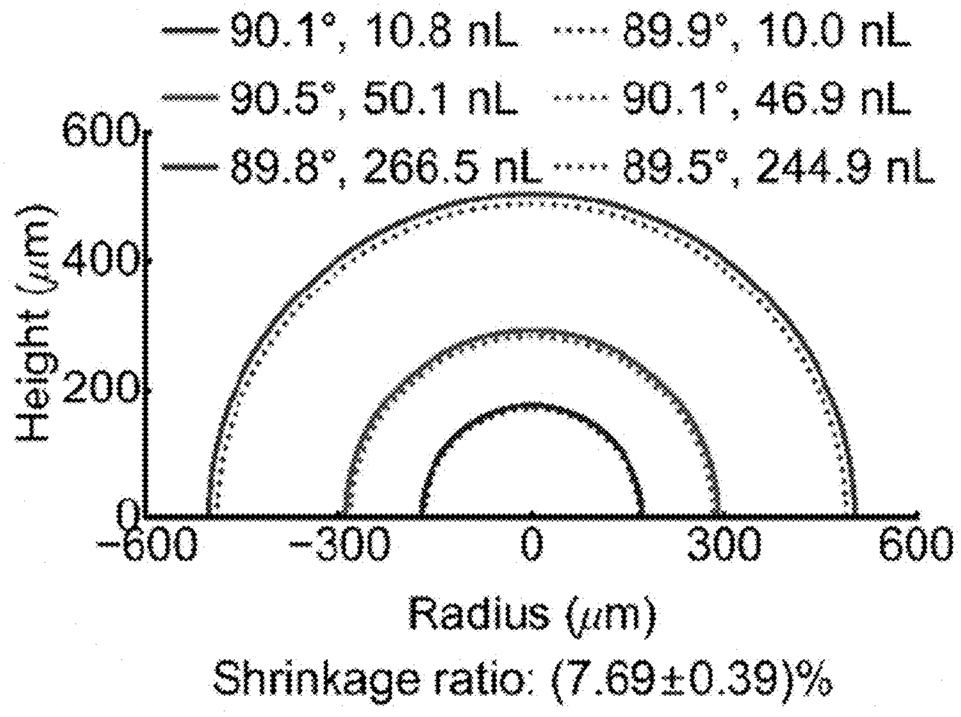

A physical boundary on a substrate can be utilized to fabricate lenses with other 3D shapes (FIGS. 1E and 1F). For instance, a spheroid lens can be fabricated using a 3D-printed circular cylinder substrate. The radius of the liquid lens and contact angle are initially governed by the substrate's wetting property and liquid volume (see the blue, purple, and red solid lines in FIG. 2D) and subsequently determined by the physical boundary size in conjunction with liquid volume (see the orange, green, and black solid lines in FIG. 2D).

The fabrication of an ellipsoid lens was validated using a 3D-printed elliptical cylinder substrate. With the increase in liquid volume, the shape and size of the lens are initially controlled by the substrate's wetting property and liquid volume (see the blue, purple, and red solid lines on x-z plane and blue and purple dashed lines on y-z plane in FIG. 2E) and then primarily by the physical boundary constraint (see the orange, green, and black solid lines on x-z plane and the red, orange, green, and black dashed lines on y-z plane in FIG. 2E). In addition, the active thermal control of the lens shape and size is also demonstrated by heating the optical liquid on the substrate with the same wettability. It can be observed that the increase in temperature leads to a decrease in contact angle and increase in radius of the lens with the same volume (see FIG. 2F).

The polymerization of lenses was performed in approximately 30 minutes using an ultraviolet (UV) lamp operating at a wavelength of around 365 nm and a power density of 65 $mW/cm^2$ (on a lens sample). A constant shrinkage ratio of 7.69% in volume was identified for the fully polymerized lenses, which kept almost unchanged contact angle and lens profile as those before polymerization (see FIG. 2G). Therefore, the calculated volume of the designed lens was increased by 8.33% to compensate for the shrinkage effect and thus achieve the desired shape and size of the polymerized lens.

Liquid-Shaped OCT Endoscope

Figure 3A:
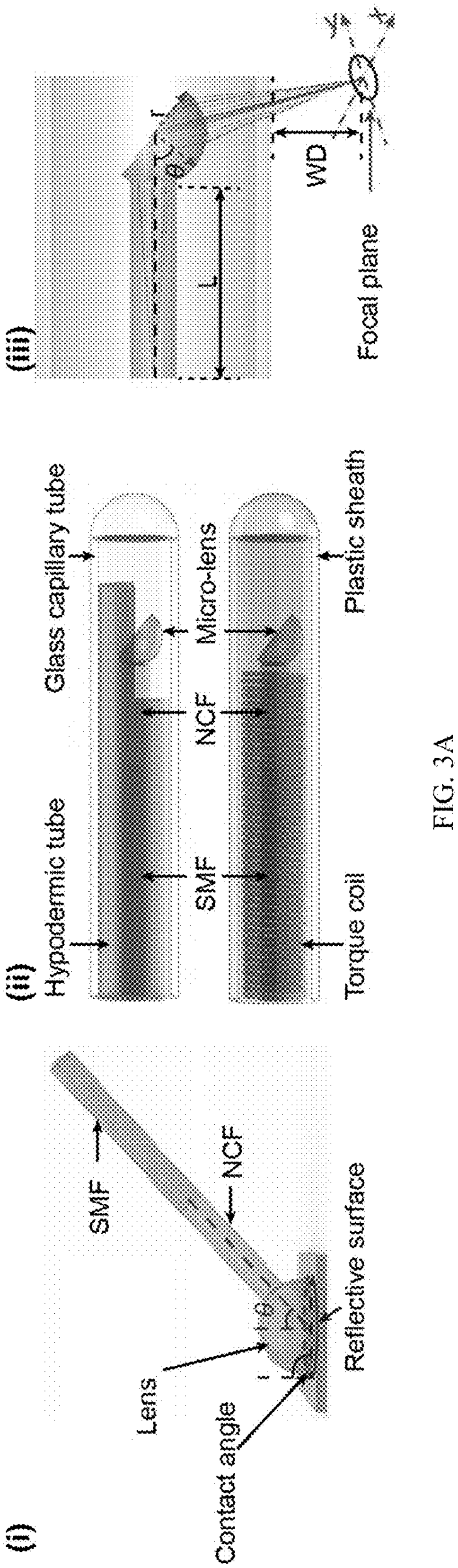
FIGS. 3A-3I depict liquid-shaped endoscope, wherein FIG. 3A(i) depicts fabrication of liquid-shaped OCT fiber probe. Optical liquid of pre-calculated volume on a glass substrate with a modified wetting property forms a lens of custom contact angle, shape, and size, which is then polymerized and used as distal optics of fiber probe made of single-mode fiber (SMF) and non-core fiber (NCF). Here an incident angle θ is formed in between the OCT light axis with respect to the normal axis of the reflective surface of lens, FIG. 3A(ii) depicts schematic of OCT endoscope. The fiber probe is guarded in a hypodermic tube (rigid version) or a torque coil (flexible version) and protected with a glass capillary tube (rigid version) or a plastic sheath (flexible version), FIG. 3A(iii) depicts zoomed-in view of the distal part of the endoscope, consisting of an NCF of length L and a semi-spherical lens of radius r and utilizing an incident angle θ. Here the working distance (WD) is measured as the normal distance between the protective sheath surface and the center of the focal plane.
Figure 3B:
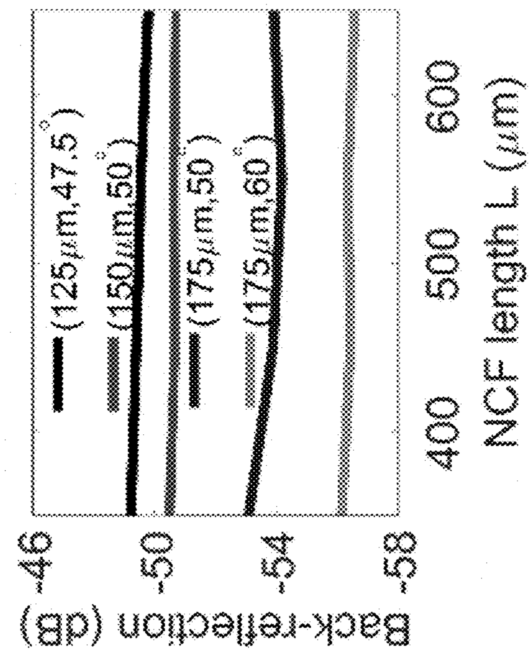
Figure 3C:
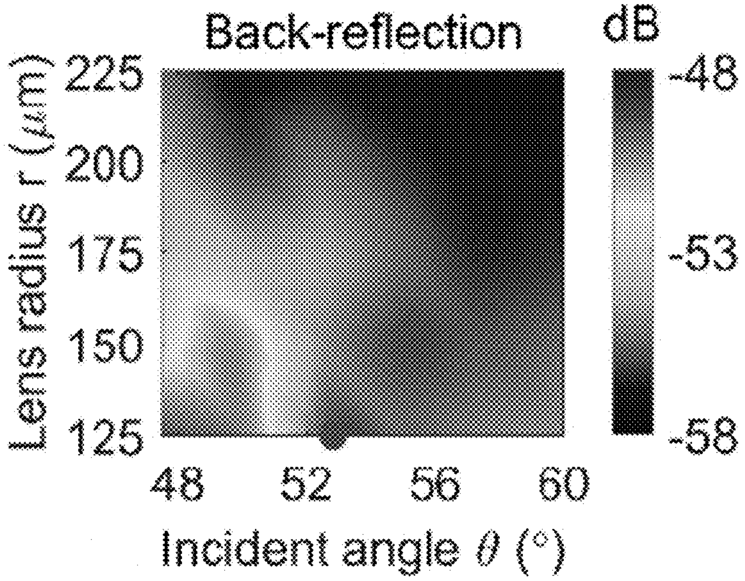
Figure 3D:
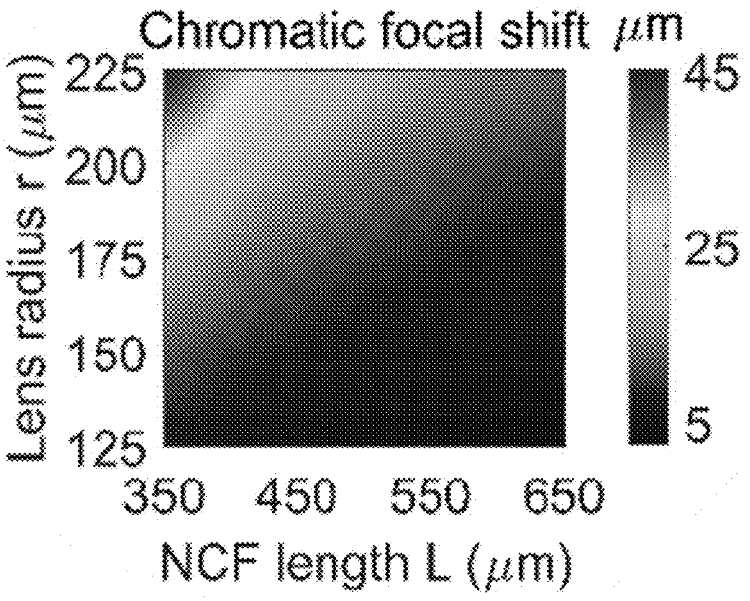
Figure 3E:
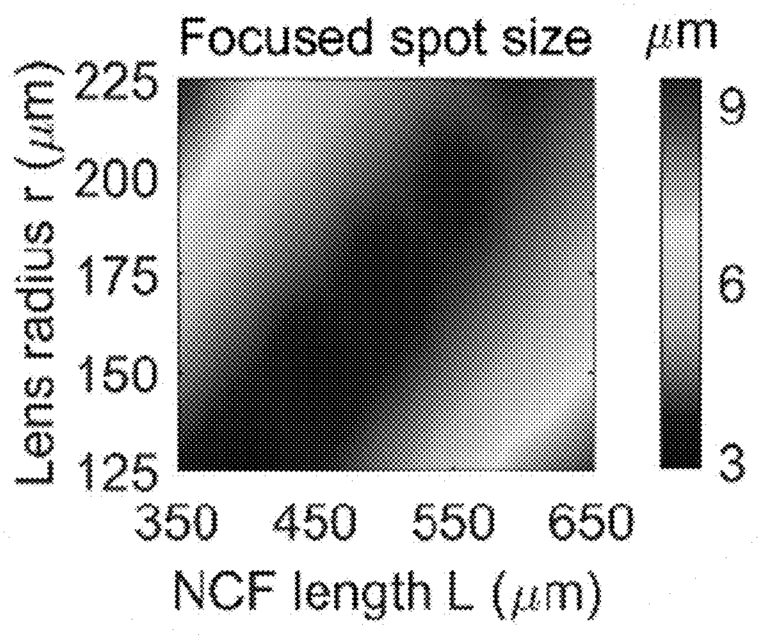
Figure 3F:
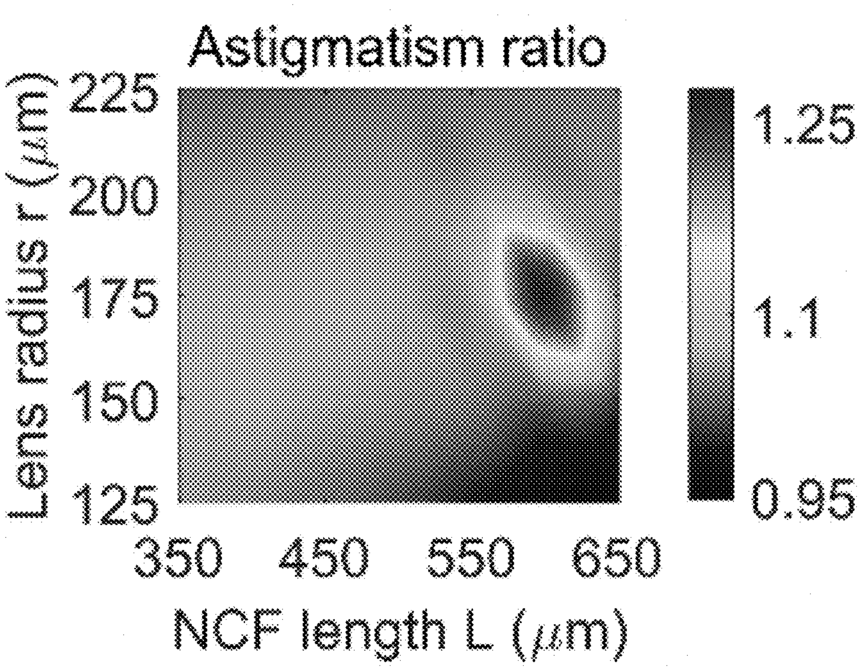
Figure 3G:
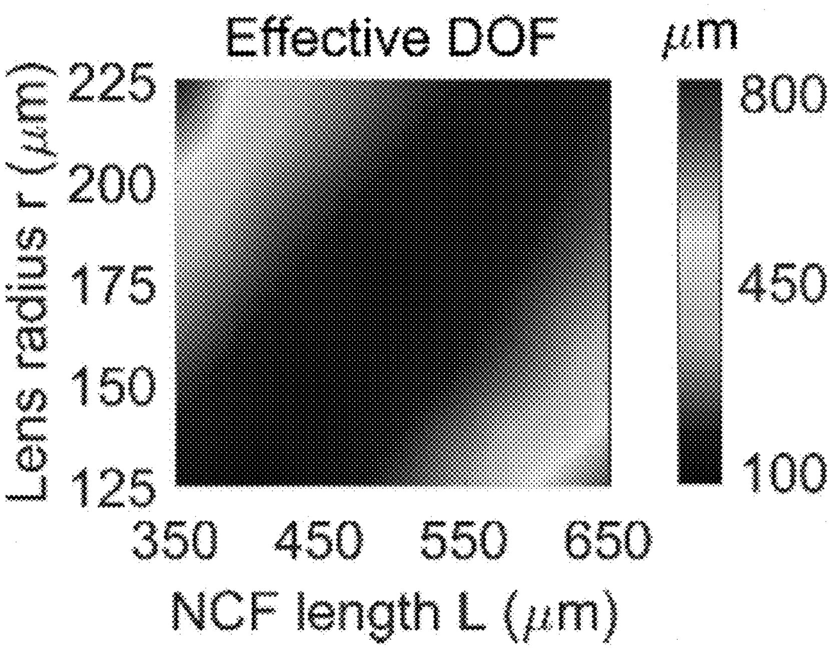
Figure 3H:
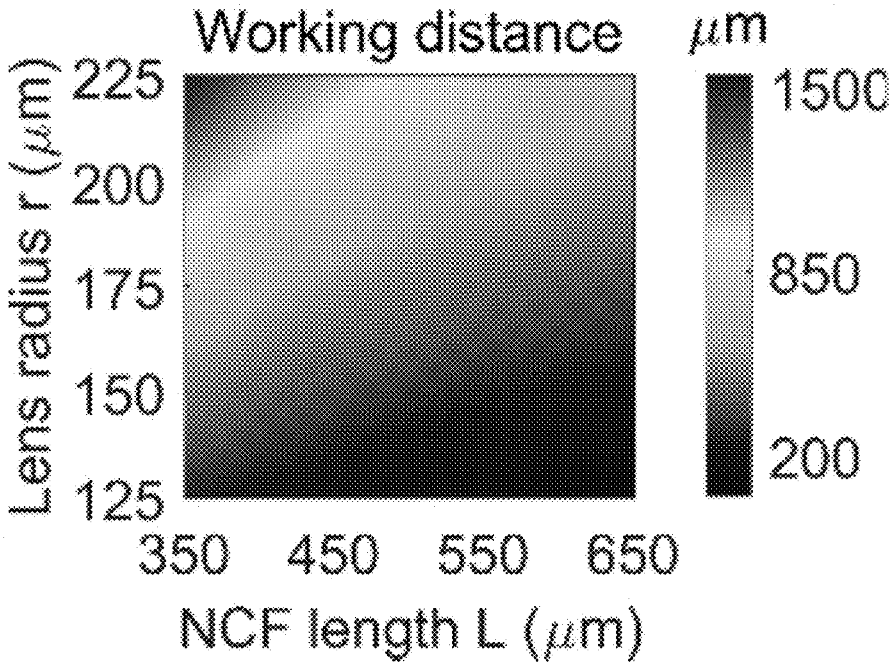
Figure 3I:
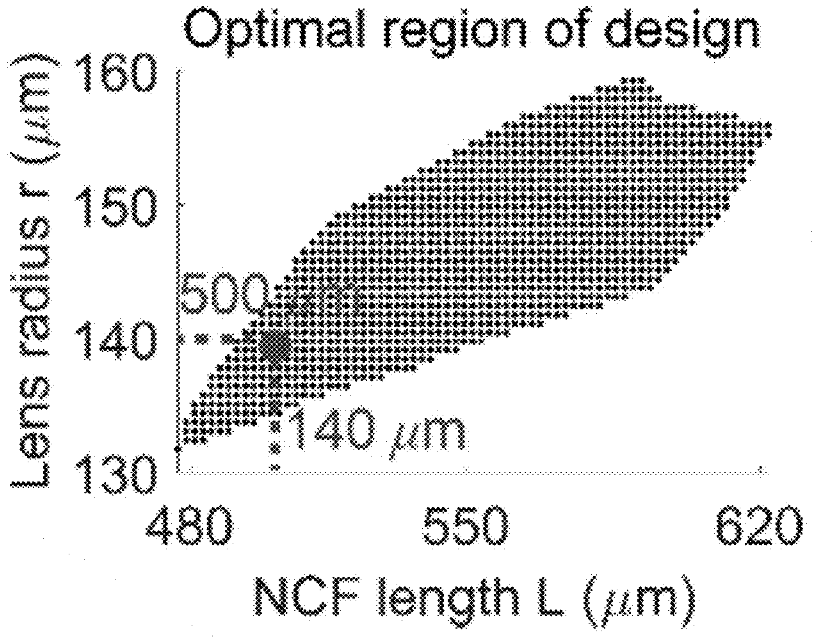

Referring to FIGS. 3A-3I, the liquid shaping technique facilitates the fabrication of an OCT fiber probe, which consists of an SMF, a non-core fiber (NCF), and a custom liquid-shaped lens (FIG. 3A(i)). Initially, an NCF piece is spliced to an SMF and then coupled to a polymerized lens at an incident angle θ by using NOA 81 as an optical adhesive. Subsequently, the OCT probe is protected with a hypodermic tube (rigid version) or a torque coil (flexible version). The entire probe is then encased in a protective sheath, such as a glass capillary tube (for the rigid version) or a plastic sheath (for the flexible version), to form an OCT endoscope (FIG. 3A(ii)). This technique enabled the scalable production and fabrication of five endoscopes simultaneously (see FIG. 4).

To demonstrate the feasibility of the liquid shaping technique for imaging performance optimization and aberration correction, a representative OCT endoscope working near 800 nm is designed using a simple semi-spherical lens (FIG. 3A(iii)). The light incident angle was initially optimized to minimize light back-reflection in the endoscope by performing stray light analysis. The total internal reflection is used with an incident angle above the critical angle (i.e., approximately 40.2° at 842 nm) on the reflective surface of the lens. The simulation results indicated that back-reflection in the OCT probe was mainly determined by the incident angle and lens radius, whereas its dependence on the NCF length was relatively low (see FIG. 3B). Generally, a larger lens radius and incident angle result in lower back-reflection in the OCT probe. As a prime example, 52.5° is selected to achieve a back-reflection of less than −56 dB for a lens radius from 125 to 150 μm (see FIG. 3C).

To further optimize imaging performance, the chromatic focus shift, focused spot size (the average spot size measured in x and y directions on the focal plane), astigmatism ratio (the ratio of spot sizes measured in x and y directions on the focal plane), effective DOF, and working distance (WD) for different combinations of NCF length and lens radius (see FIGS. 3D-3H) are calculated. Compiling the simulated results indicated an optimal design region (see FIG. 3I) that provides optimal imaging performance, such as a chromatic focal shift of less than 6 μm, a focused spot size (i.e., transverse resolution) of less than 6 μm, an astigmatism ratio between 0.9 and 1.1, an effective DOF of larger than 150 μm, and a WD of between 200 and 300 μm. A design that involves fabricating a liquid-shaped endoscope using a 500-μm-long NCF is used, a lens with a 140-μm radius, and an incident angle of 52.5°. This approach enables achromatic performance to be achieved with a minimal focal shift of approximately 5.4 μm, a high transverse resolution of approximately 4.6 μm, a low astigmatism ratio of approximately 1.05 on the focal plane, a low back-reflection of less than −56 dB, and an appropriate DOF and WD of approximately 197.3 μm and 238 μm, respectively (see FIG. 3I).

Figure 4:
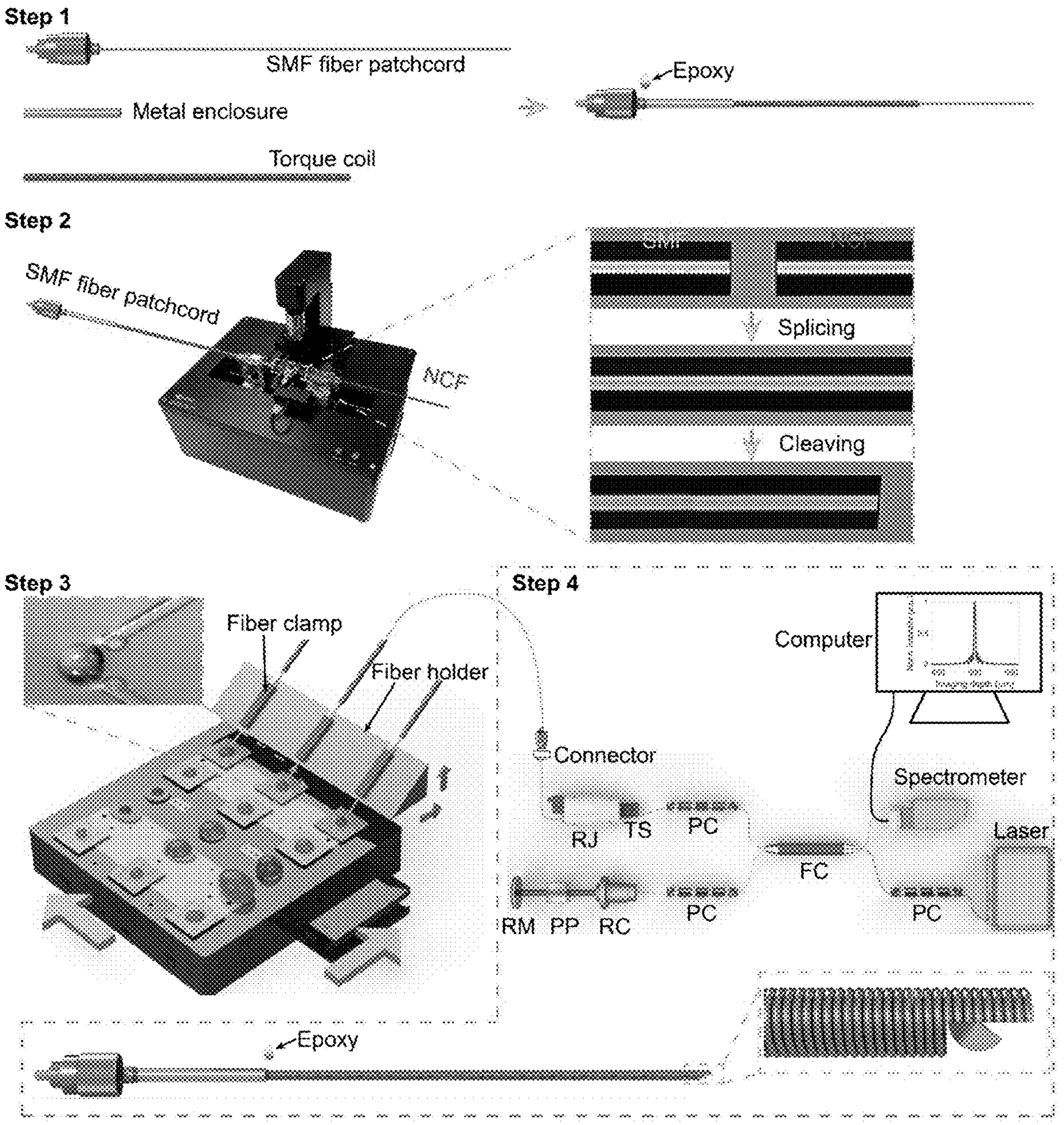
FIG. 4 depicts development of a part-count-reduction fiber endoscope assembly system with passive alignment and in-line quality check features, in accordance with some embodiments of the subject invention.

Development of a Part-Count-Reduction Fiber Endoscope Assembly System with Passive Alignment and in-Line Quality Check Features Referring to FIG. 4, a part-count-reduction design in OCT endoscope is implemented and a fiber endoscope assembly system is developed including passive alignment and in-line quality check features. The OCT endoscope adopts a monolithic optical fiber design and only needs 5 parts, including a single mode fiber (SMF) (780HP, Thorlabs Inc.), a non-core fiber (NCF) (FG125LA, Thorlabs Inc.), a custom liquid-shaped lens, a short piece of stainless-steel tube, and a torque coil with distal side opening (FIG. 4). Compared with the conventional OCT endoscopes, the uses of distal hypodermic tube, the GRIN lens, glass spacer, and mirror reflector are reduced. Such a part-count-reduction endoscope design greatly simplifies the endoscope fabrication procedures to 4 steps, including, Step 1: gluing stainless-steel tube to SMF and sleeving SMF in a torque coil with distal side opening in 5 minutes; Step 2: splicing SMF to NCF and cleaving NCF to a predetermined length in 5 minutes; Step 3: coupling fiber to a polymerized freeform lens at an incident angle θ by using optical adhesive and curing the optical adhesive in 10 minutes; Step 4: Online checking of assembly quality and sleeving down and gluing torque coil in 10 minutes (see FIG. 4).

For Step 2, a Vytran automated glass processor (GPX3800, Thorlabs Inc.) with integrated cleaver will be used to perform SMF/NCF splicing and inline NCF cleaving. For Step 3, the passive alignment features in assembly system include the use angulated v-groove to help couple fiber to freeform lens at angle θ and the use of integrated OCT module for quick control of the fiber-lens distance. By implementing multiple angulated v-groove modules in parallel, the production of endoscopes is scaled up.

A spectral domain OCT module using SLD as light source and spectrometer as detector will be developed and integrated into endoscope assembly system for quick examination of the endoscope quality (FIG. 4), including one-way throughput (at least 90%), back reflection (less than −55 dB), point spread function (i.e., axial resolution), focused spot size (i.e., transverse resolution), and test the imaging quality on a standard phantom. In addition, using the distance ranging function, the same OCT module will be used to control the fiber-lens distance during the endoscope assembly.

Characterization of the OCT Endoscopes

Figure 5A:
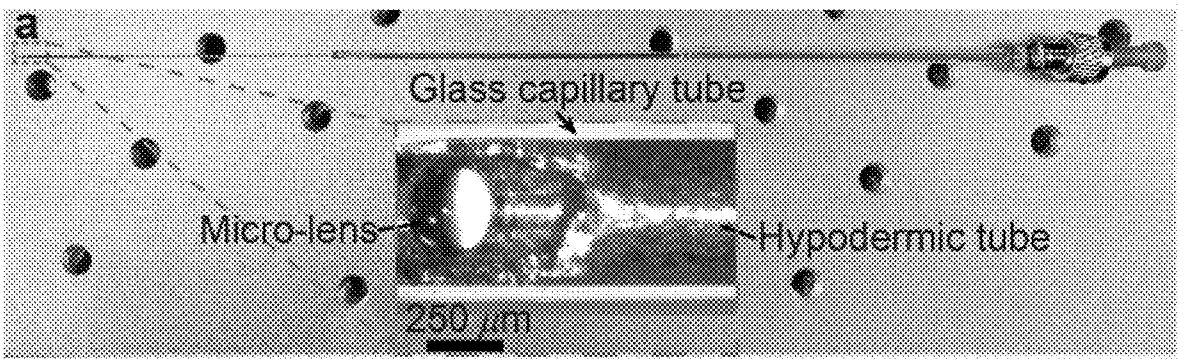
Figure 5B:
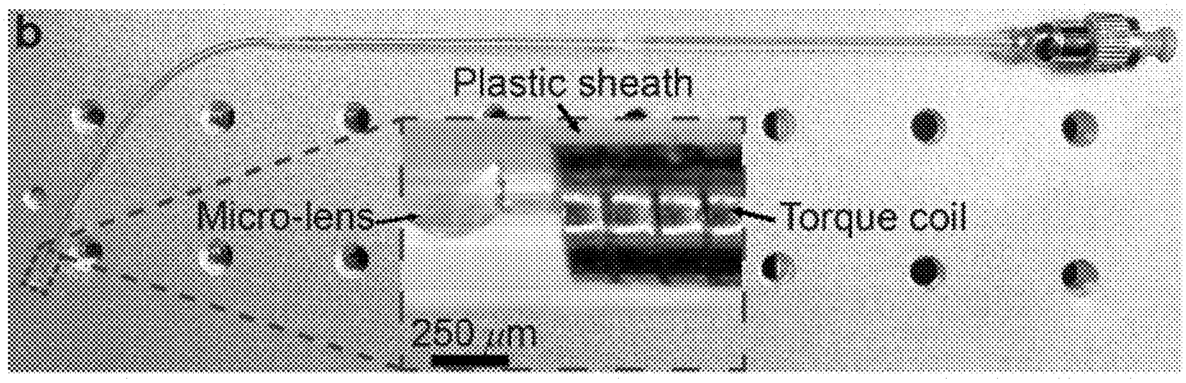
Figure 5C:
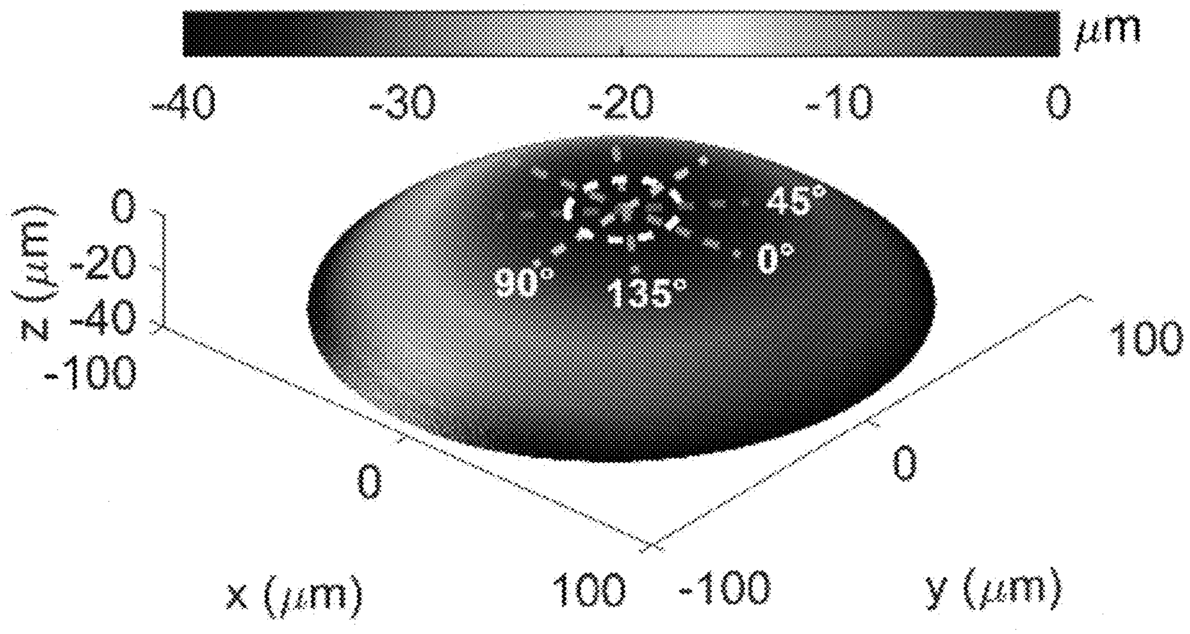
Figure 5D:
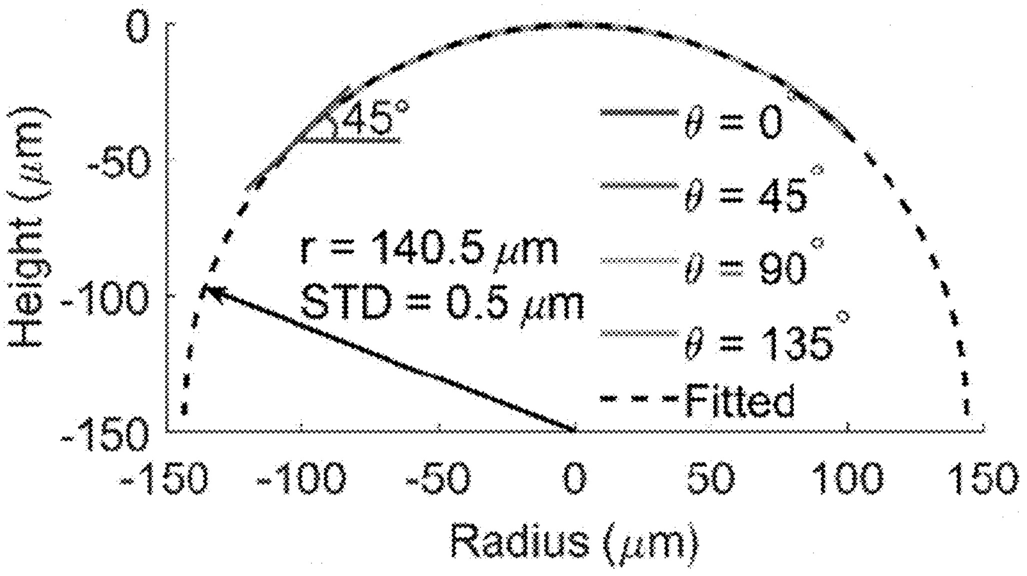
Figure 5E:
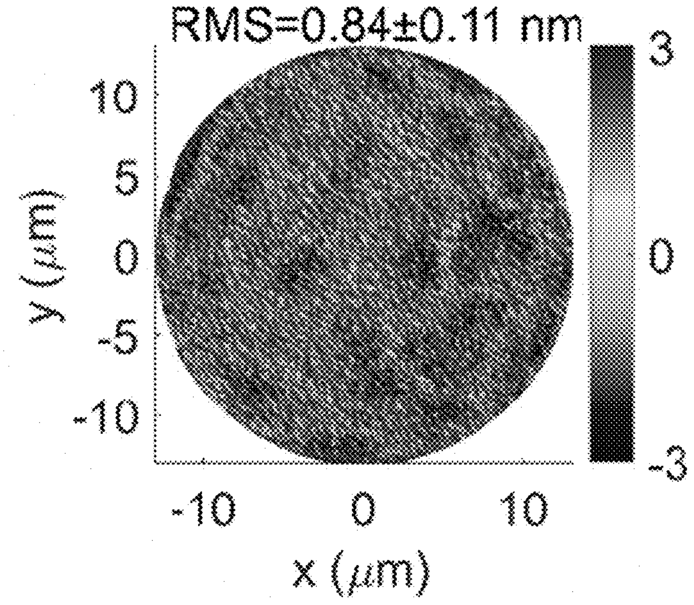
Figure 5F:
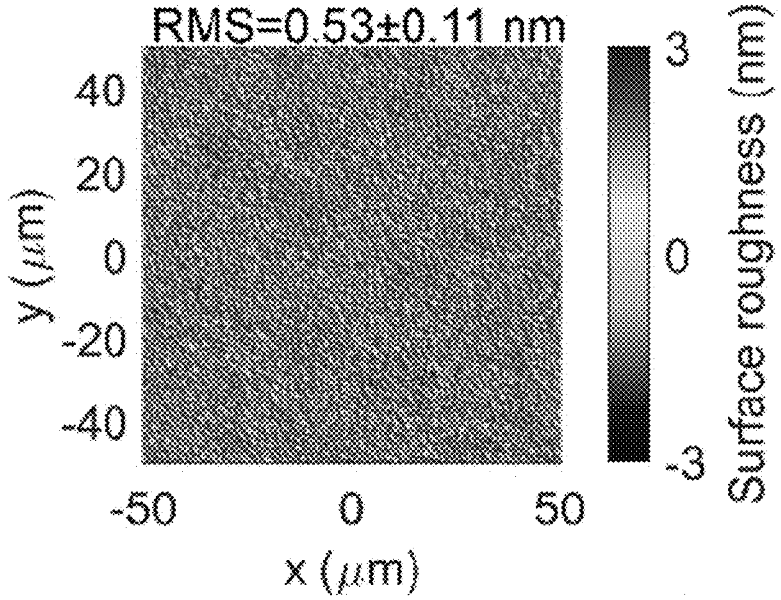
Figure 5G:
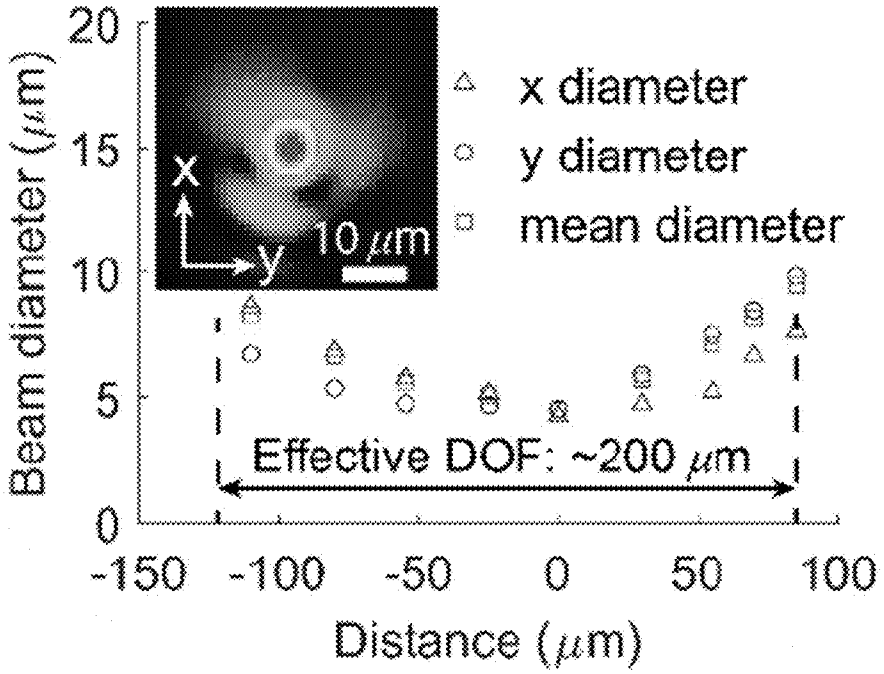
Figure 5H:
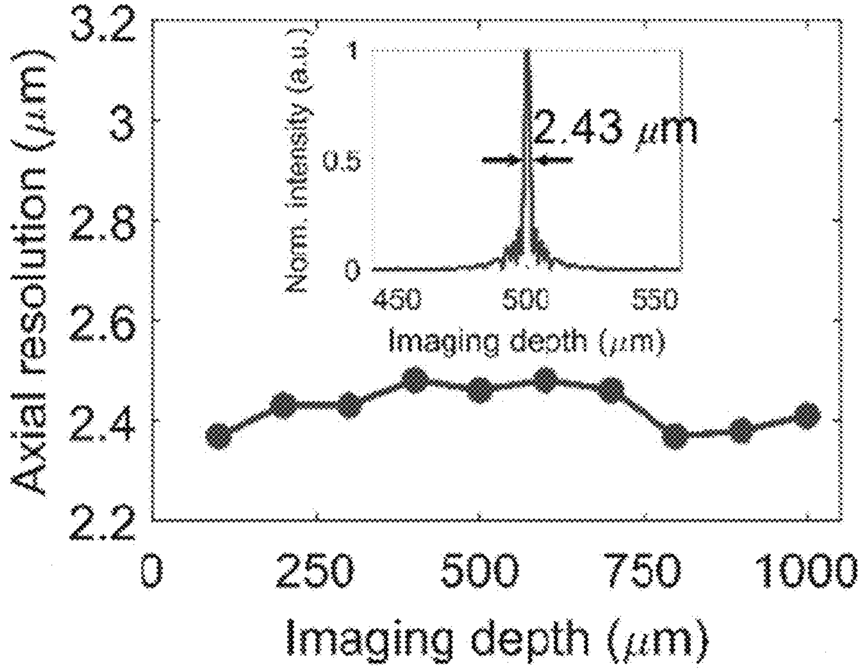
Figure 5I:
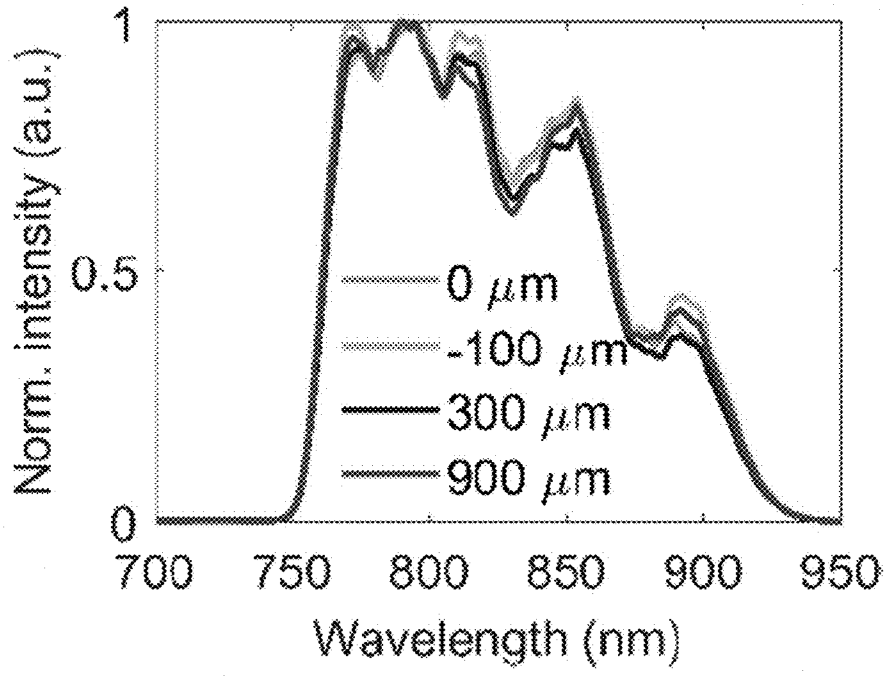

Both the rigid and flexible versions of liquid-shaped OCT endoscopes, with diameters of approximately 0.6 mm (including a protective sheath), were fabricated using the aforementioned probe design (see FIGS. 5A and 5B). Five endoscopes were simultaneously fabricated in 90 minutes, with comparable results, demonstrating the scalability of the method of the subject invention (see FIGS. 4 and 10). To illustrate the fabrication quality and controllability of the liquid shaping technique, the surface profile of the distal semi-spherical lens was first characterized using a 3D non-contact confocal surface profiler (MarSurf CM Expert, Mahr Inc.). Because the profiler's imageable slope angle was limited to only approximately 45°, only the top 40-μm height of the lens (FIG. 5C) is measured. The fitted one-dimensional surface profiles at four radial angles (i.e., 0°, 45°, 90°, and 135°) indicated a lens of a symmetric semi-spherical shape with a radius of approximately 140.5±0.5 μm (close to the designed radius of 140 μm), suggesting the precise control of lens shape and size (see FIG. 5D). Using a white-light interferometry-based surface profiler (MarSurf WI 50, Mahr Inc.), the surface roughness of the lens on the top curved surface to be 0.84±0.11 nm (see FIG. 5E) is measured. This sub-nanometer roughness is due to the smoothness of the liquid-air interface in the liquid shaping technique. Meanwhile, a surface roughness of 0.53±0.11 nm on the flat reflective surface of the lens is noted, owing to the use of an ultra-flat glass substrate (see FIG. 5F). A liquid-shaped lens with sub-nanometer surface roughness enables the effective mitigation of unwanted light scattering in the distal focusing optics of the OCT endoscope.

To further characterize endoscopes, a spectral-domain OCT (SD-OCT) system is constructed (see FIG. 11). The diameter of the OCT laser beam exiting the protective sheath, such as the glass capillary tube used in the rigid endoscope, was measured in both x and y directions along the light-emitting direction using an optical beam profiler (BladeCam2-XHR, DataRay Inc., FIG. 5G). The smallest focused spot was measured approximately 240 μm away from the outer sheath surface, exhibiting spot sizes of about 4.5 and 4.3 μm in x and y directions, respectively (with a mean diameter of 4.5 μm, inset of FIG. 5G), indicating a low astigmatism ratio of 1.05 on the focal plane. These measurements align well with the simulated focused spot size of 4.6 μm at a working distance of 238 μm. Furthermore, the measured effective DOF was approximately 200 μm, which was estimated by polynomial-fitting the mean beam diameters within the depth range where the beam diameter was smaller than twice the size of the focused spot. Additionally, the achromaticity of the endoscope was verified based on the observation of less than 5% variation in the axial resolution of approximately 2.43 μm along the 1-mm imaging depth (see FIG. 5H) and confirmed by the nearly unchanged back-reflected spectra measured by moving a mirror along the light-emitting direction (see FIG. 5I). These results demonstrated the ultrahigh resolution of the liquid-shaped OCT endoscope.

Ultrahigh-resolution Imaging of Luminal Organs Referring to FIGS. 6A-6D, the flexible endoscope is advantageous in terms of its mechanical flexibility, and ultrahigh resolution. It can pass through the constricted lumen, such as narrowed sections in the blood vessels, and smoothly scan small luminal organs, such as an infant's esophagus. The endoscope enables the detection of fine microstructures and subtle pathologies of diseased tissues in vivo. In this study, a rat's esophagus was imaged to evaluate the imaging performance of the endoscope. The probe initially traveled through the oral cavity of the rat, passed the pharynx, traversed the tight upper esophageal sphincter (a narrow luminal structure that facilitates swallowing and reduces food backflow into the pharynx), and finally reached the section of the gastroesophageal junction (GEJ). 3D volumetric imaging was performed at a speed of 10 frames/second over a 36-mm-long esophagus. A separation of adjacent frames, i.e., pitch number, of 20 μm was used to control the pullback speed of the endoscope.

The reconstructed 3D image revealed the GEJ section of the rat's esophagus (see FIG. 6A). A representative OCT cross-section clearly delineated the layered microstructure of the esophagus near the GEJ (see FIG. 6B). The fine laminar structures of the esophagus, including the stratified squamous epithelium (EP), lamina propria (LP), muscularis mucosae (MM), submucosa (SM), circular muscle (CM), and longitudinal muscle (LM), were clearly observed in a zoomed-in view (see FIG. 6C). The microstructures of the esophagus observed on the OCT image aligned with the corresponding hematoxylin and eosin (H&E) histology micrograph (see FIG. 6D).

In Situ Imaging of Lumens in Complex Internal Organs

Currently, the accurate assessment of high-risk arterial diseases, such as atherosclerosis, in small vessels remains challenging due to their narrow lumens, highly complex networks, and vast distribution. Thus, a flexible endoscope that allows for minimally invasive and ultrahigh-resolution imaging in small blood vessels is highly desirable. To evaluate the functionality of the endoscope in the blood vessels, the in situ imaging of the descending aorta is performed in a normal mouse model.

Referring to FIGS. 7A-7G, the mouse was first euthanized by administering an overdose of ketamine and xylazine before imaging. The mouse heart and connected vessels were perfused with phosphate-buffered saline using a 27-gauge needle inserted into the apex of left ventricle. This perfusion procedure depleted blood in the aorta, thereby preventing any interference from high-scattering red blood cells during OCT imaging. Subsequently, the endoscope was inserted through the left femoral artery. It passed through the descending abdominal aorta and thoracic aorta sections, finally reaching the section close to the aortic arch (see FIG. 7A).

A 14.6-mm-long section of the descending thoracic aorta was imaged at a speed of 10 frames/second with a frame pitch of 20 μm (see FIG. 7B). The imaged aorta was then excised, fixed, embedded, sectioned into 10-μm-thick slices, and stained with H&E. As demonstrated in the OCT cross-section, the zoomed-in view, and the corresponding histology micrograph, the laminar microstructures of the mouse aorta, including the tunica intima (TI), Tunica Media™, tunica adventitia (TA), and adipose tissues (AT) is clearly observed (see FIGS. 7C-7E). Furthermore, multiple elastic lamellae (EL, with high scattering) intermixed with smooth muscle sheets were identified in the TM layer.

The ultrahigh-resolution imaging facilitated by the endoscope enabled the clear delineation and accurate quantification of the microstructures of the aorta for the in situ evaluation of arterial diseases. A preliminary study revealed that in a normal mouse, the thicknesses of the aortic layers were 11.0±1.2, 69.2±3.4, and 28.2±2.2 μm for the TI, TM, and TA, respectively (see FIG. 7F). In particular, the TI, which is the thinnest and innermost layer of an artery or vein, is composed of a single layer of endothelial cells; its thickening and proliferation are considered an early indication of atherosclerosis.

Interstitial Imaging in Deep Brain In Vivo

Referring to FIGS. 8A-8I, the rigid endoscope of small size can extend the limited imaging depth of OCT and perform high-resolution, volumetric interstitial imaging of solid organs. This facilitates the access and evaluation of deep-seated diseases, such as deep brain tumors, ischemic stroke, and epilepsy, while minimizing the risks of hemorrhage and other trauma caused by probe insertion.

To evaluate the functionality of the rigid endoscope, in vivo deep-brain imaging is performed in a mouse brain. After making an incision on the scalp, two small burr holes are drilled on each of the two contralateral sides of the skull (see FIG. 8A). The endoscope was then inserted through the burr holes into the deep brain, following an insertion trajectory perpendicular to the brain surface (see FIG. 8B). A 5-mm-long (in z direction) cylindrical deep brain volume was imaged in 50 seconds at a speed of 10 frames/second. Because of the ultrahigh resolution of the endoscope, mouse brain structures, including the cerebral cortex, corpus callosum, caudate putamen, and ventral striatum, are clearly observed on the 3D volumetric image (see FIG. 8C). The en face projection view, generated by summing the unfolded cylindrical brain volume along the imaging depth, revealed the distinct laminated brain structures of the mouse, which were also verified in the histology micrograph, indicating a good correlation between the OCT representation and histomorphology (see FIGS. 8D-8E and 12). Representative OCT cross-sections acquired at different depths illustrate the detailed morphological features of each mouse brain structure (see FIGS. 8F-8I). In particular, the filament bundle structures of striatopallidal fibers in the caudate putamen were clearly observed on the OCT images (see FIGS. 8C, 8D, and 8H).

Discussion

An OCT endoscope with a high resolution and large DOF is necessary for the accurate imaging of subtle pathological changes in tissues. For this purpose, an appropriately designed lens is required in the endoscope. However, it is difficult to precisely tailor a lens by using the fiber melting technique. To overcome this limitation, the liquid shaping technique is provided. This method allows for the precise customization of the shape and size of a liquid droplet on a substrate, thereby producing a freeform lens with an ultrasmall form factor, corrected aberrations, and desired imaging performance. These features can be achieved by conveniently modifying the wettability of a substrate, controlling the liquid volume, and utilizing physical constraints on the substrate. In contrast to the 3D printing method, the technique does not require expensive high-end machinery and can be easily scaled up. Additionally, the liquid shaping technique yields a custom lens with a sub-nanometer surface roughness (see FIG. 5), which is considerably better than the roughness (approximately 10-200 nm) achieved using the two-photon 3D printing.

The liquid shaping technique offers a novel approach to simultaneously fabricate high-performance cost-effective OCT endoscopes. The fabrication process of the endoscope involves only standard and common optical fiber handling procedures, such as splicing and cleaving, and the simple gluing of a custom lens to the fiber probe tip (see FIG. 4). These processes can be streamlined for mass production. This approach eliminates the need for a time-consuming angle-polishing process that is required in conventional GRIN fiber and fiber ball-lens-based methods. The use of the approach substantially reduces both fabrication time and cost and increases the yield rate due to the minimized reliance on human expertise. Furthermore, the longitudinal study revealed that the fabricated endoscopes maintain their imaging performance over a long period (see FIGS. 13A-13D). Thus, the liquid-shaped endoscope can serve as a low-cost and disposable OCT catheter for translational use.

Our liquid-shaped OCT endoscope can be fitted in different clinical applications such as blood vessels of different sizes, while maintaining high imaging performance. In principle, the form factor of the endoscope fabricated using the liquid shaping technique can be further minimized using a thinner hypodermic tube or torque coil and a smaller protective sheath over the entire probe. The imaging performance of a downsized endoscope can be optimized by customizing a smaller lens with appropriate back-reflection, achromaticity, astigmatism ratio, resolution, and DOF (see FIG. 3). Likewise, the form factor of the endoscope can be increased to image larger lumens (e.g., those with a diameter greater than 2 mm) by fabricating an appropriately designed lens. In contrast, it would be suboptimal to fabricate a fiber ball-lens-based microprobe to image lumens larger than 2 mm because a microprobe with a longer working distance tends to lead to a degraded transverse resolution and, more importantly, an increased longitudinal focal shift.

Although the fabrication of 800-nm OCT endoscopes using the liquid shaping technique is provided as a representative example, the technique is not confined to this wavelength. The versatility of the liquid shaping technique allows for the fabrication of OCT endoscopes operating at various other wavelengths. For instance, it can accommodate the 1,300 nm range, which is prevalent in most existing cardiovascular OCT imaging systems. Additionally, it can function within the visible light range and the 1,700 nm range.

Methods

Liquid Droplet Generation and Characterization

A piezoelectrically actuated dispenser (SA306, Sans Inc.) was utilized for droplet/lens generation. This technique was reported in previous works and widely used for microarray printing, tissue engineering, and fabrication of functional materials. To account for the system dispensing accuracy, the calibration of the dispensed liquid volume on the substrate was first performed (FIG. 14). A series of liquid volumes claimed by the dispenser was dispensed on the glass substrate to form the liquid lens; the contact angle, dimensions, and volume of lens were then measured using a liquid drop analysis system (OCA 25, Dataphysics Instruments GmbH) at room temperature of 25° C. and analyzed with SCA 20 software (DataPhysics Instruments GmbH). After calibration, the liquid lens volume can be controlled at a precision of about 0.1 nL. The accuracy of contact angle measurement is ±0.1°, the accuracy of length measurement is ±0.5 μm, and the accuracy of volume measurement is ±0.05 nL.

As for the polymerized lens, the contact angle, dimensions, and volume were characterized using the same method as liquid lens, while the lens profile was measured using a confocal surface profiler (MarSurf CM Expert, Mahr Inc.) and its surface roughness was characterized with a white-light interferometry-based surface profiler (MarSurf WI 50, Mahr Inc.).

Surface Wettability Modification of Glass Substrate

Glass substrates (S2006A1, Ossila) used in the study provide a super-polished surface of about 1-nm roughness. To modify the surface wettability, the glass substrate is first treated in oxygen plasma bathing for 10 minutes. The substrate is then placed in a petri dish and soaked in the mixture of fluoride (volume: 10-20 μL) and solvent (volume: 10 mL). The petri dish is sealed and placed in a fume hood at room temperature for 4 to 16 hours to achieve desired surface wettability and contact angle on the substrate (see Table 1). After that, the glass substrate is retrieved and thoroughly rinsed with absolute ethanol before use.

TABLE 1

Six Groups of Glass Substrates with Different Parameters of Surface Wettability Modification

| Glass substrate group | Processing time [a] | Volume of fluoride | Contact angle |
|---|---|---|---|
| Glass substrate 1 | 0 hour | 0 μL | ~50° |
| Glass substrate 2 | 4 hours | 10 μL | ~67° |
| Glass substrate 3 | 6 hours | 10 μL | ~75° |
| Glass substrate 4 | 8 hours | 10 μL | ~85° |
| Glass substrate 5 | 12 hours | 10 μL | ~90° |
| Glass substrate 6 | 16 hours | 20 μL | ~110° |

[a] The processing time indicates the period when the sample is soaked in the fluoride solution.

The Fabrication and Surface Wettability Modification of Cylinder Substrates

A stereolithography 3D printer (S300, nanoArch) was employed to fabricate cylinder substrates of circular or elliptical boundary with an about 400-μm height. Polyethylene Glycol Diacrylate (PEGDA) was used for 3D printing.

To modify the surface wettability, the cylinder substrate is first processed with oxygen plasma bathing for 10 minutes. Then, it is placed in a petri dish with the cylinder top surface immersed in 10 μL of fluoride. The petri dish is sealed with Kapton tape and placed in a thermotank with a baking temperature of 100° C. for 4 to 8 hours to achieve desired surface wettability and contact angle on the substrate (see Table 2). After that, the cylinder substrate is retrieved and thoroughly rinsed with absolute ethanol before use.

TABLE 2

Two Groups of Cylinder Substrates with Different Parameters of Surface Wettability Modification

| Cylinder substrate group | Processing time [a] | Volume of fluoride | Contact angle [b] |
|---|---|---|---|
| Circular cylinder substrate | 4 hours | 10 μL | ~65° |
| Elliptical cylinder substrate | 8 hours | 10 μL | ~80° |

[a] The processing time indicates the period when the sample is baked in a thermotank for fluorination.

[b] The contact angle is measured when the lens is not constrained by the physical boundary.

Fabrication of Liquid-Shaped Lens

The procedures to fabricate lens using liquid shaping technique are illustrated in FIGS. 8A and 8B. Specifically, NOA 81 was selected over other optical liquids in this study. The NOA 81 liquid was first degassed in a vacuum chamber (98 kPa vacuum level for 10 minutes) to remove any potential micro-bubbles. Then, the liquid of calculated volume was dispensed using the piezoelectrically actuated dispenser (SA306, Sans Inc.) on wettability-modified glass substrate or circular/elliptical cylinder substrates. The desired shape of size of lens is obtained by precisely controlling liquid volume, wettability, and physical boundary of substrate.

After that, the liquid lens on substrate was degassed again in a vacuum chamber (98 kPa vacuum level for 10 minutes). Finally, the liquid lens was polymerized by using a UV lamp illumination for 30 minutes to ensure complete polymerization, which usually only needs 20 minutes. The UV lamp has a center wavelength of about 365 nm and provides power density of 65 mW/cm$^2$ on the lens sample. It should be noted that a polymerization-induced shrinkage effect of optical liquid (about 7.69%, see FIG. 2G) was considered and pre-compensated in volume calculation during the lens fabrication. For the endoscopes demonstrated in current work, the lens liquid with a volume of about 6.2 nL was dispensed on the substrate to fabricate the semi-spherical lens of about 140-μm radius and contact angle of about 89.8°.

Zemax Simulations

OpticStudio (v17, Zemax LLC) was used to design and optimize the liquid-shaped endoscope. The refractive index profiles and material dispersions of silica (of NCF) and NOA 81 are considered in simulations (see FIG. 15). The back-reflection under different incident angles, lens radii, and NCF lengths was first calculated using stray light analysis in the non-sequential mode. After that, the ray-tracing simulation of the endoscope was performed in the mixed sequential/non-sequential mode. By considering a single-mode fiber with numerical aperture of 0.13, the chromatic focal shift, focused spot size, astigmatism ratio, effective DOF, and working distance were calculated under different lens radii and NCF lengths.

Animal Studies and Histological Correlation

The protocol of OCT endoscopic imaging in rat and mouse was approved by the Laboratory Animal Services Centre at The Chinese University of Hong Kong.

For rat esophagus (n=4, Sprague Dawley rats) and mouse aorta (n=4, nude mice) imaging, animals were euthanized by overdosing of ketamine (100 mg/kg) and xylazine (16 mg/kg) before OCT imaging. The flexible endoscope was first deployed near to rat GEJ section and mouse aortic arch, respectively. Then, OCT pullback imaging was performed at a speed of 10 frames/second. The endoscope probe was retreated after imaging, while the plastic sheath was left in the lumens for registration of the imaged tissues. The imaged esophagus and aorta were harvested and fixed in formalin together with plastic sheath overnight before being submitted for histological processing. Standard H&E slides were obtained and correlated with OCT imaging results.

For deep brain imaging (n=4, nude mice), the mouse anesthetization was first introduced by intraperitoneal injection of ketamine (100 mg/kg) and xylazine (16 mg/kg) and further maintained by inhaling 2% isoflurane with medical oxygen. Burr holes (about 1 mm in diameter) were made on two contralateral sides of mouse skull to allow the deployment of rigid endoscope (see FIG. 8A). The burr hole location was selected to avoid major blood vessels. Before insertion, a thin needle (with a diameter of about 300 μm) was utilized to introduce a small hole through the pia mater. The endoscope was then inserted through the burr hole into the mouse brain with a slow speed of about 10 μm/s. After imaging, the mouse was sacrificed and the brain was immediately harvested. A glass capillary tube was inserted back into the brain tissue along the same imaging trajectory, helping register the imaged tissue. The brain tissue together with glass capillary was then placed in formalin for 48 hours. After fixation, the brain tissue was divided into two sections (see FIG. 16) for further histological processing. Standard H&E slides were obtained and correlated with en face OCT images.

Shrinkage of Lenses Before and After Polymerization

There is a scale-invariable shrinkage of the liquid-shaped lens after the complete polymerization, which keeps the contact angle and shape unchanged. To study the shrinkage ratio of NOA 81-based lens, a 365-nm ultraviolet lamp was used to provide a power density of 65 mW/cm$^2$ (on lens sample). The volumes of the lens before ($V_1$) and after ($V_2$) polymerization were measured using a liquid drop analysis system (OCA 25, Dataphysics Instruments GmbH) at room temperature of 25° C. As shown in Table 3 below, the average shrinkage ratio in volume (defined as $$\frac{V_1 - V_2}{V_1}\Big)$$

) is found to be about 7.69% with a standard deviation of 0.39% for NOA 81-based lens.

TABLE 3

Volume variation of lenses before and after polymerization.

| Volume before exposure ($V_1$, nL) | Volume after exposure ($V_2$, nL) | Shrinkage ratio $\left(\frac{V_1 - V_2}{V_1}\right)$ | Averaged shrinkage ratio |
|---|---|---|---|
| 1841.4 | 1712.0 | 7.03% | 7.69% ± 0.39% |
| 1521.7 | 1393.5 | 8.43% | |
| 1263.7 | 1176.0 | 6.93% | |

TABLE 3-continued

Volume variation of lenses before and after polymerization.

| Volume before exposure ($V_1$, nL) | Volume after exposure ($V_2$, nL) | Shrinkage ratio $\left(\frac{V_1 - V_2}{V_1}\right)$ | Averaged shrinkage ratio |
|---|---|---|---|
| 765.6 | 712.2 | 6.93% | |
| 658.5 | 607.6 | 7.73% | |
| 470.7 | 430.1 | 8.62% | |
| 266.5 | 244.9 | 8.12% | |
| 213.3 | 197.3 | 7.51% | |
| 149.7 | 138.1 | 7.74% | |
| 51.1 | 46.8 | 8.41% | |
| 28.6 | 26.4 | 7.34% | |
| 10.8 | 10.0 | 7.41% | |

Therefore, an increase of 8.33% of the calculated volume of the designed lens is used to compensate for the shrinkage effect to help achieve the desired shape and size of the polymerized lens. As for the lens used in endoscopes, the dispensed liquid volume was about 6.2 nL to achieve a semi-spherical lens of a radius of 140 μm and lens volume of about 5.7 nL.

Characterization and Imaging Results of Simultaneously Fabricated Liquid-Shaped Endoscopes Five endoscopes were simultaneously fabricated, including two rigid ones (#1 and #2') and three flexible ones (#3, #4, and #5). They were characterized of similar results (see Table 4 below) and tested for OCT imaging (see FIGS. 10A-10E) with comparable image qualities, showing the scalability of the liquid shaping technique for endoscope fabrication.

TABLE 4

Characterization of the simultaneously fabricated liquid-shaped endoscopes.

| Characterized parameter | # 1* | # 2 | # 3** | # 4 | # 5 |
|---|---|---|---|---|---|
| x focused spot size | 4.5 μm | 4.6 μm | 4.5 μm | 4.7 μm | 4.5 μm |
| y focused spot size | 4.3 μm | 4.4 μm | 4.3 μm | 4.5 μm | 4.2 μm |
| Mean focused spot size [a] | 4.5 μm | 4.6 μm | 4.5 μm | 4.7 μm | 4.4 μm |
| Astigmatism ratio | 1.05 | 1.05 | 1.05 | 1.04 | 1.07 |
| Effective DOF | 200 μm | 202 μm | 198 μm | 204 μm | 196 μm |
| Working distance | 240 μm | 235 μm | 241 μm | 237 μm | 243 μm |
| Mean axial resolution [b] | 2.43 μm | 2.52 μm | 2.43 μm | 2.45 μm | 2.51 μm |
| Axial resolution variation [c] | 4.6% | 4.7% | 4.6% | 5.0% | 4.8% |
| Mean spectral variation [d] | 0.0136 | 0.0141 | 0.0138 | 0.1315 | 0.0145 |

*The reported rigid endoscope.

**The reported flexible endoscope.

[a] Mean focused spot size = 0.83114 × x + 0.16886 × y when x ≥ y, mean focused spot size = 0.16886 × x + 0.83114 × y when x < y, and x and y indicate the beam diameters in x and y directions, respectively.

[b-c] The axial resolution is measured every 100 μm along the imaging depth of 100 μm to 1000 μm, and mean axial resolution and axial resolution variation can be calculated.

[d] The mean spectral variation (MSV) is calculated by MSV = MEAN(STD(S1, S2, . . . , Si)), where Si is a 2048 × 1 vector that contains the normalized spectral data, MEAN is the averaging operation, and STD indicates the standard deviation.

Ultrahigh-Resolution Endoscopic SD-OCT System

To characterize the performance of the endoscope, a homemade endoscopic spectral-domain OCT (SD-OCT) system was built (see FIG. 11). The custom SD-OCT system employed a superluminescent diode source (MT-850-HP, Superlum Inc.) with a 3-dB bandwidth of 160 nm and a central wavelength of about 842 nm. A 50:50 fiber coupler (TW850R5A2, Thorlabs Inc.) was adopted to split the light into the reference and sample arms. The light beam in the reference arm was collimated using a reflective collimator (RC02APC-P01, Thorlabs Inc.). A pair of N-SF11 prisms (Edmund Inc.) were inserted between the reflective collimator and the reflective mirror (PF05-03-P01, Thorlabs Inc.) to compensate for the dispersion imbalance between the reference and sample arms. A homemade rotary joint was mounted on a linear translational stage (X-LSM150A, Zaber Technologies) to rotate and pull back the imaging probe and thus obtain three-dimensional volumetric images. The OCT light back-reflected from reference and sample arms interferences with each other and is collected using a spectrometer (Cobra-S 800, Wasatch Photonics Inc.) with a high line-scan rate up to 250 kHz. To manage the polarization mode dispersion (PMD), two polarization controllers (FPC030, Thorlabs Inc.) are utilized. The imaging depth of the system is about 1.04 mm.

Choice of Optical Liquids for Lens Fabrication

Six representative optical liquids, including NOA 60, NOA 61, NOA 63, NOA 65, NOA 68, and NOA 81 (Norland Products Inc.), have been considered to fabricate the lens (see Table 5). NOA 81 is selected because of (1) fast curing property (20 minutes UV light exposure at a power density of 65 mW/cm$^2$ for complete polymerization); (2) good endurance against temperature variation (withstand −150~125° C. after polymerization); (3) its low viscosity, which makes it easy to dispense; (4) relatively high elastic modulus, which makes it tough and not easy to deform; and (5) relatively high transmission near 800 nm (as high as 96%).

TABLE 5

| Comparison between optical liquids | | | | | |
|---|---|---|---|---|---|
| Optical liquid | Cure Time [a] | Working Temperature [b] | Viscosity @ 25° C. [c] | Elastic Modulus [d] | Transmission @ VIS to NIR [e] |
| NOA60 | 25 minutes | −15~90° C. | 300 cps | 135000 psi | 96% |
| NOA61 | 25 minutes | −150~125° C. | 300 cps | 150000 psi | 96% |
| NOA63 | 40 minutes | −15~90° C. | 2000 cps | 240000 psi | 98% |
| NOA65 | 40 minutes | −15~60° C. | 1200 cps | 20000 psi | 98% |
| NOA68 | 40 minutes | −80~90° C. | 5000 cps | 20000 psi | 98% |
| NOA81 | 20 minutes | −150~125° C. | 300 cps | 200000 psi | 96% |

[a]-[e] The data are obtained from Norland Product Inc.

Comparison with Existing Fabrication Methods and Commercial Products

Currently, there are three methods (i.e., conventional methods) for fabricating disposable OCT endoscopes: (1) the gradient-index (GRIN) lens/fiber-based method, (2) the fiber ball-lens-based method, and (3) the single or two-photon 3D printing-based method (see Table 6).

(1) The GRIN lens/fiber-based method uses the commercially available GRIN lens and fiber to build the OCT endoscope. However, there are limited choices of GRIN lenses and GRIN fibers, limiting the optimization of imaging performance. This method involves a complex discrete-sectional assembly and requires precise and time-consuming optical alignment. In addition, the use of GRIN lens/fiber introduces strong chromatic and spherical aberrations in near-infrared and visible light regimes, compromising the axial and transverse resolutions of OCT endoscope. Using GRIN fiber, a polishing procedure is needed to fabricate a reflector on fiber tip for beam redirection. Such polishing procedure is costly and time-consuming, and the resultant reflector usually has a suboptimal surface roughness.

(2) The fiber ball-lens-based method uses an electric arc or filament to melt the fiber and create a ball-lens on the fiber tip, i.e., the fiber melting technique. Such method has been demonstrated to fabricate a monolithic OCT endoscope of achromatic performance. However, an angle polishing procedure is required in this method to fabricate a reflective surface on ball-lens for beam redirection. Such polishing procedure is costly and time-consuming, and the resultant reflector usually has a suboptimal surface roughness. The fiber melting technique also lacks sufficient controllability to customize the ball-lens and optimize its imaging performance.

(3) The single or two-photon 3D printing method is capable of directly producing freeform optics on fiber tip to fabricate monolithic OCT endoscopes. However, the printed optics suffer from suboptimal optical surface roughness ranging from 10 to 200 nm, causing undesired light scattering which may degrade the OCT imaging performance. Considering the additive manufacturing nature and the expensive 3D printer, this method is costly and not scalable.

Unlike the conventional methods, the method (i.e., liquid shaping-based method) fabricates the high-performance OCT endoscope using liquid shaping technique, i.e., liquid-shaped OCT endoscope, in less than 1.5 hours. The method enables (1) the mass production of freeform optics of sub-nanometer surface roughness and customized imaging performance in less than 30 mins, and (2) the fast and automated assembly of OCT endoscopes of monolithic design and customized specifications in parallel in less than 60 mins. The liquid shaping technique-based methods provide excellent controllability and ample flexibility to fabricate custom freeform optics. The automated fabrication system eliminates the need of lens polishing and high-precision optical alignments.

TABLE 6

| Comparison of conventional and liquid shaping-based fabrication methods | | |
|---|---|---|
| Methods | Pros | Cons |
| GRIN lens/fiber-based method | 1. GRIN lens and fiber commercially available. | 1. limited choice of GRIN lens and GRIN fiber.<br>2. Requires precise and time-consuming optical alignment.<br>3. Strong chromatic and spherical aberrations at short wavelength regimes, such as 800 nm and visible light.<br>4. Requires costly and time-consuming angle-polishing.<br>5. Suboptimal surface roughness due to polishing.<br>6. Fabrication time of about 3 hours.<br>7. Fabrication cost of about $120. |
| Fiber ball-lens-based method | 1. Monolithic design.<br>2. Miniature size.<br>3. Achromatic performance. | 1. Insufficient design freedom and controllability on ball-lens using fiber melting technique.<br>2. Spherical aberration degrades resolution.<br>3. Requires costly and time-consuming angle-polishing.<br>4. Suboptimal surface roughness due to polishing. |

TABLE 6-continued

| Comparison of conventional and liquid shaping-based fabrication methods | | |
|---|---|---|
| Methods | Pros | Cons |
| | | 5. Limited to fabricate achromatic endoscopes of less than 1 mm in diameter.<br>6. Fabrication time of about 4 hours.<br>7. Fabrication cost of about $80. |
| Single/two-photon 3D printing-based method | 1. Monolithic design.<br>2. Freeform lens of high design freedom for aberration corrections. | 1. Suboptimal surface roughness.<br>2. Lack of scalability potential.<br>3. High fabrication cost<br>4. Fabrication time of 5 hours, depending on the lens size.<br>5. Fabrication cost of about $500. |
| Liquid shaping-based method | 1. Monolithic design.<br>2. Freeform optics (lens and mirror) of high design freedom for aberration corrections.<br>3. Mass production of freeform optics.<br>4. Freeform optics of sub-nanometer surface roughness.<br>5. No need for lens polishing and precise optical alignment.<br>6. Scalable fabrication.<br>7. Fabrication time of 1.5 hours.<br>8. Fabrication cost of about $70. | NA |

TABLE 7

| The performance and price of commercial versus liquid-shaped endoscopes for cardiovascular OCT systems | | | | |
|---|---|---|---|---|
| | Dragonfly OpStar ™ Imaging Catheter, Abbott | Fastview ™ Coronary Imaging Catheter, Terumo | LumenCross ® F2, Vivolight | Liquid-shaped OCT endoscope |
| Fabrication method | Fiber ball-lens-based method | GRIN fiber-based method | Fiber ball-lens-based method | Liquid shaping method |
| Operation wavelength | 1.3 μm | 1.3 μm | 1.3 μm | Customizable, including near-infrared light (1.3 μm, 1 μm, 0.8 μm) and visible light (~0.55 μm) |
| Axial resolution | 10-15 μm | 10-20 μm | ~15 μm | Customizable, smallest ~ 1 μm |
| Transverse resolution | 20-40 μm | 20-40 μm | 35-75 μm | Customizable |
| Imaging depth in tissue | ~3 mm | ~3 mm | ~3 mm | Customizable, 1-3 mm |
| Diameter | 2.0-3.5 mm | ~0.9 mm | ~1 mm | Customizable, smallest ~0.3 mm |
| Price | $2,598 | $2,650 | $2,018 | $70 (targeted price, see Table 8 for cost breakdown) |

TABLE 8

| The fabrication cost of liquid-shaped OCT endoscope | |
|---|---|
| Components | Cost |
| Fiber patchcord | $10 |
| Torque coil | $50 |
| Optical liquid | $ 1 |
| Protective sheath | $ 4 |
| Other consumables and machining | $ 5 |
| | $70 in total |

Benefits of Disposable Cardiovascular OCT Endoscopes

The disposable OCT endoscope, i.e., liquid-shaped OCT endoscope, aims to offer low-cost and high-performance options to the current cardiovascular OCT market players. This presents several benefits to patients and healthcare providers:

a. Low adoption costs with increased patient accessibility and benefits: the mass production of liquid-shaped OCT endoscopes can greatly reduce the adoption cost of OCT endoscopy in clinic and provide a competitive advantage to OCT over IVUS in terms of both imaging performance and cost.

b. Improved patient safety and outcome: Disposable endoscopes can help minimize the risk of cross-contamination and infection associated with reusable endoscopes, thereby enhancing patient safety and reducing the likelihood of hospital-acquired infections. Furthermore, the customization of disposable OCT endoscopes for individual patients, such as varying catheter sizes to accommodate different vessel dimensions, as well as adjustments in resolution capabilities and imaging depth in tissue, can better address diagnostic and interventional needs, leading to improved patient outcomes.

In one embodiment, a method for scalable production of freeform optical lenses based on a liquid shaping technique is provided, comprising forming a liquid-shaped lens by dispensing a curable optical liquid on a substrate and curing, wherein a surface of the substrate is pre-processed to have pre-determined wettability within a pre-designed region, wherein the curable optical liquid is dispensed within the pre-designed region on the substrate, forming a liquid polymer lens, and wherein the liquid polymer lens is dispensed to have a pre-determined size and a pre-determined shape within the pre-designed region on the substrate; and polymerizing the liquid polymer to form the liquid-shaped lens.

In one embodiment, the polymerizing comprises exposing to UV light and heating.

In one embodiment, the size and the shape of the liquid-shaped lens is freeform and actively configuring the pre-designed region with specific wettability and controlling a volume of the curable optical liquid that fills the pre-designed region.

In one embodiment, the actively configuring the pre-designed region comprises performing surface wettability modification methods including a passive method of chemical processing, or active modification methods including thermal control and electromagnetic field control of the surface wettability.

In one embodiment, the liquid-shaped lens has a sub-nanometer surface roughness.

In one embodiment, the production of the liquid lens is performed simultaneous with production of multiple liquid-shaped lenses of various shapes and sizes without increasing production time.

In one embodiment, a high-performance optical coherence tomography (OCT) endoscope system fabricated based on a liquid shaping technique is provided, comprising an OCT imaging probe comprising a single-mode fiber; a beam-delivery element spliced to the single-mode fiber; and an aberration-correction liquid-shaped lens fabricated with a liquid shaping technique, wherein the liquid-shaped lens is configured to have a predetermined size, a predetermined shape, being bonded at an end of the beam-delivery element with a predetermined length so as to reduce chromatic aberration, spherical aberration, and astigmatism of the OCT imaging probe and achieve high axial and transverse resolutions, wherein the liquid-shaped lens is coupled at the end of the beam-delivery element with a pre-determined alignment angle for beam redirection and focusing, and wherein the liquid-shaped lens is coupled at the end of the beam-delivery element, the liquid-shaped lens fabricated using an optical liquid and subsequently polymerized thereby forming the lens; and a protective metal enclosure, the OCT imaging probe with predetermined size being fitted within the protective metal enclosure and protected by a transparent housing to define a high-performance OCT endoscope, wherein the protective metal enclosure has a pre-cut opening on a cylindrical surface thereof that acts as a beam passage window.

In one embodiment, the beam-delivery element comprises a non-core fiber or a multi-mode fiber.

In one embodiment, the polymerization comprises any of: UV light exposure, drying, and heating.

In one embodiment, distal optics of the liquid-shaped OCT lens have a sub-nanometer surface roughness to reduce strong scattering in short wavelengths and enhance image quality.

In one embodiment, the liquid-shaped lens is configured to have a high transmission and low back reflection over a broad spectral range. The high transmission is denoted as a large percentage, for example, a percentage greater than 95%, of optical power being transferred through the lens. The low back reflection is a small portion, for example, a value smaller than −55 in decibel, of optical power being reflected back by the lens. The broad spectral range is denoted as a large bandwidth of the chromatic light, for example, in a range of 400-700 nm, or in a range of 650-950 nm, or in a range of 1265-1380 nm.

In one embodiment, the broad spectral range includes a range from visible light to near-infrared light.

In one embodiment, the system is configured for fabrication of multiple liquid-shaped OCT imaging probes that are carried out simultaneously for mass fabrication.

In one embodiment, a method for scalable production of freeform optical mirrors based on a liquid shaping technique is provided, comprising fabricating a mirror fabricated by dispensing a curable liquid in a pre-defined shape in a container and curing the liquid to define the mirror, wherein the container has a predetermined dimension and a predetermined boundary; wherein the curable liquid is dispensed depending on a pre-calculated volume and is dispensed by a high-precision dispenser into the container, wherein a freeform shape of an upper surface of the dispensed curable liquid in the container is determined by a volume of the liquid and the container boundary, and wherein a body of the mirror is defined by the cured liquid; and coating the cured liquid in the predetermined dimension and the predetermined boundary with a highly reflective metal or dielectric layer so as to define an outer reflective surface of the mirror.

In one embodiment, the curing comprises polymerizing that comprises any of: exposure to UV light, drying, and heating.

In one embodiment, the polymerized liquid-shaped mirror has a sub-nanometer surface roughness.

In one embodiment, the liquid-shaped mirror is either detached from the container or attached.

In one embodiment, a high-performance optical coherence tomography (OCT) endoscope system fabricated based on a liquid shaping technique is provided, comprising a single-mode fiber; a beam-delivery element spliced to the single-mode fiber for delivery of a light beam therethrough; and an aberration-corrected mirror fabricated with the liquid shaping technique; wherein the beam-delivery element delivers the light beam to the mirror; wherein the aberration-corrected liquid-shaped mirror is configured to have a desired freeform reflective surface for beam redirection and focusing, and wherein the mirror and the beam-delivery element are positioned in a protective metal enclosure, and protected by a transparent housing, forming the high-performance OCT imaging endoscope, and wherein the protective metal enclosure is pre-cut with an opening on a cylindrical surface thereof that acts as a beam passage window.

In one embodiment, the beam-delivery element comprises any of a non-core fiber, a multi-mode fiber, and a fiber ball-lens.

In one embodiment, the mirror has a freeform reflective surface formed by liquid shaping and disposed at a predetermined tilted angle to redirect and focus the light beam.

In one embodiment, the tiled angle is determined, at least in part, by a boundary shaped of a 3D printed container in which the liquid is deposited.

In one embodiment, the beam delivery element and the mirror are configured to reduce a chromatic aberration, spherical aberration, and astigmatism of the high-performance OCT imaging probe and achieve high axial and transverse resolutions.

In one embodiment, the mirror is configured to have a high reflectivity and low back reflection over a broad spectral range.

In one embodiment, the broad spectral range includes a range from visible light to near-infrared light.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms “comprising,” “including,” and “having,” as used herein, are specifically intended to be read as open-ended terms of art. Any references to publication, patents, or patent applications are incorporated herein by reference in their entirety for all purposes.

Exemplary Embodiments

Embodiments of the subject invention include, but are not limited to, the following exemplified embodiments:

Embodiment 1. A method for scalable production of freeform optical lenses based on a liquid shaping technique, comprising:

forming a liquid-shaped lens by dispensing a curable optical liquid on a substrate and curing, wherein a surface of the substrate is pre-processed to have pre-determined wettability within a pre-designed region, wherein the curable optical liquid is dispensed within the pre-designed region on the substrate, forming a liquid polymer lens, and wherein the liquid polymer lens is dispensed to have a pre-determined size and a pre-determined shape within the pre-designed region on the substrate; and polymerizing the liquid polymer to form the liquid-shaped lens.

Embodiment 2. The method of embodiment 1, wherein the polymerizing comprises exposing to UV light and heating.

Embodiment 3. The method of embodiment 1, wherein the size and the shape of the liquid-shaped lens is freeform and further comprising actively configuring the pre-designed region with specific wettability and controlling a volume of the curable optical liquid that fills the pre-designed region.

Embodiment 4. The method of embodiment 3, wherein the actively configuring the pre-designed region comprises performing surface wettability modification methods including a passive method of chemical processing, or active modification methods including thermal control and electromagnetic field control of the surface wettability.

Embodiment 5. The method of embodiment 1, wherein the liquid-shaped lens has a sub-nanometer surface roughness.

Embodiment 6. The method of embodiment 1, wherein the production of the liquid lens is performed simultaneous with production of multiple liquid-shaped lenses of various shapes and sizes without increasing production time.

Embodiment 7. A high-performance optical coherence tomography (OCT) endoscope system fabricated based on a liquid shaping technique, comprising:

an OCT imaging probe comprising:

a single-mode fiber;

a beam-delivery element spliced to the single-mode fiber; and an aberration-correction liquid-shaped lens fabricated with a liquid shaping technique, wherein the liquid-shaped lens is configured to have a predetermined size, a predetermined shape, being bonded at an end of the beam-delivery element with a predetermined length so as to reduce chromatic aberration, spherical aberration, and astigmatism of the OCT imaging probe and achieve high axial and transverse resolutions, wherein the liquid-shaped lens is coupled at the end of the beam-delivery element with a pre-determined alignment angle for beam redirection and focusing, and wherein the liquid-shaped lens is coupled at the end of the beam-delivery element, the liquid-shaped lens fabricated using an optical liquid and subsequently polymerized thereby forming the lens; and a protective metal enclosure, the OCT imaging probe with predetermined size being fitted within the protective metal enclosure and protected by a transparent housing to define a high-performance OCT endoscope, wherein the protective metal enclosure has a pre-cut opening on a cylindrical surface thereof that acts as a beam passage window.

Embodiment 8. The system of embodiment 7, wherein the beam-delivery element comprises a non-core fiber or a multi-mode fiber.

Embodiment 9. The system of embodiment 7, wherein the polymerization comprises any of: UV light exposure, drying, and heating.

Embodiment 10. The system of embodiment 7, wherein distal optics of the liquid-shaped OCT lens have a sub-nanometer surface roughness to reduce strong scattering in short wavelengths and enhance image quality.

Embodiment 11. The system of embodiment 7, wherein the liquid-shaped lens is configured to have a high transmission and low back reflection over a broad spectral range.

Embodiment 12. The system of embodiment 11, wherein the broad spectral range includes a range from visible light to near-infrared light.

Embodiment 13. The system of embodiment 7, wherein the system is configured for fabrication of multiple liquid-shaped OCT imaging probes that are carried out simultaneously for mass fabrication.

Embodiment 14. A method for scalable production of freeform optical mirrors based on a liquid shaping technique, the method comprising:

fabricating a mirror fabricated by dispensing a curable liquid in a pre-defined shape in a container and curing the liquid to define the mirror, wherein the container has a predetermined dimension and a predetermined boundary; wherein the curable liquid is dispensed depending on a pre-calculated volume and is dispensed by a high-precision dispenser into the container, wherein a freeform shape of an upper surface of the dispensed curable liquid in the container is determined by a volume of the liquid and the container boundary, and wherein a body of the mirror is defined by the cured liquid; and coating the cured liquid in the predetermined dimension and the predetermined boundary with a highly reflective metal or dielectric layer so as to define an outer reflective surface of the mirror.

Embodiment 15. The method of embodiment 14, wherein the curing comprises polymerizing that comprises any of: exposure to UV light, drying, and heating.

Embodiment 16. The method of embodiment 14, wherein the polymerized liquid-shaped mirror has a sub-nanometer surface roughness.

Embodiment 17. The method of embodiment 14, wherein the liquid-shaped mirror is either detached from the container or attached.

Embodiment 18. A high-performance optical coherence tomography (OCT) endoscope system fabricated based on a liquid shaping technique, comprising:

a single-mode fiber;

a beam-delivery element spliced to the single-mode fiber for delivery of a light beam therethrough; and an aberration-corrected mirror fabricated with the liquid shaping technique;

wherein the beam-delivery element delivers the light beam to the mirror;

wherein the aberration-corrected liquid-shaped mirror is configured to have a desired freeform reflective surface for beam redirection and focusing, and wherein the mirror and the beam-delivery element are positioned in a protective metal enclosure, and protected by a transparent housing, forming the high-performance OCT imaging endoscope, and wherein the protective metal enclosure is pre-cut with an opening on a cylindrical surface thereof that acts as a beam passage window.

Embodiment 19. The system of embodiment 18, wherein the beam-delivery element comprises any of a non-core fiber, a multi-mode fiber, and a fiber ball-lens.

Embodiment 20. The system of embodiment 18, wherein the mirror has a freeform reflective surface formed by liquid shaping and disposed at a predetermined tilted angle to redirect and focus the light beam.

Embodiment 21. The system of embodiment 20, wherein the tiled angle is determined, at least in part, by a boundary shaped of a 3D printed container in which the liquid is deposited.

Embodiment 22. The system of embodiment 18, wherein the beam delivery element and the mirror are configured to reduce a chromatic aberration, spherical aberration, and astigmatism of the high-performance OCT imaging probe and achieve high resolution.

Embodiment 23. The system of embodiment 18, wherein the mirror is configured to have a high reflectivity and low back reflection over a broad spectral range.

Embodiment 24. The system of embodiment 23, wherein the broad spectral range includes a range from visible light to near-infrared light.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A high-performance optical coherence tomography (OCT) endoscope system fabricated based on a liquid shaping technique, comprising:

an OCT imaging probe comprising:

a single-mode fiber;

a beam-delivery element spliced to the single-mode fiber; and an aberration-correction liquid-shaped lens fabricated with a liquid shaping technique, wherein the liquid-shaped lens is configured to have a predetermined size, a predetermined shape, being bonded at an end of the beam-delivery element with a predetermined length so as to reduce chromatic aberration, spherical aberration, and astigmatism of the OCT imaging probe and achieve high axial and transverse resolutions, wherein the liquid-shaped lens is coupled at the end of the beam-delivery element with a pre-determined alignment angle for beam redirection and focusing, and wherein the liquid-shaped lens is coupled at the end of the beam-delivery element, the liquid-shaped lens fabricated using an optical liquid and subsequently polymerized thereby forming the lens; and a protective metal enclosure, the OCT imaging probe with predetermined size being fitted within the protective metal enclosure and protected by a transparent housing to define a high-performance OCT endoscope, wherein the protective metal enclosure has a pre-cut opening on a cylindrical surface thereof that acts as a beam passage window.

2. The system of claim 1, wherein the beam-delivery element comprises a non-core fiber or a multi-mode fiber.

3. The system of claim 1, wherein the polymerization comprises any of: UV light exposure, drying, and heating.

4. The system of claim 1, wherein distal optics of the liquid-shaped OCT lens have a sub-nanometer surface roughness to reduce strong scattering in short wavelengths and enhance image quality.

5. The system of claim 1, wherein the liquid-shaped lens is configured to have a high transmission and low back reflection over a broad spectral range.

6. The system of claim 5, wherein the broad spectral range includes a range from visible light to near-infrared light.

7. The system of claim 1, wherein the system is configured for fabrication of multiple liquid-shaped OCT imaging probes that are carried out simultaneously for mass fabrication.

* * * * *